United States Patent
Bosl et al.

(10) Patent No.: US 10,278,608 B2
(45) Date of Patent: May 7, 2019

(54) DETECTION OF EPILEPTOGENIC BRAINS WITH NON-LINEAR ANALYSIS OF ELECTROMAGNETIC SIGNALS

(71) Applicant: Children's Medical Center Corporation, Boston, MA (US)

(72) Inventors: William J. Bosl, Brookline, MA (US); Tobias Loddenkemper, Somerville, MA (US)

(73) Assignee: Children's Medical Center Corporation, Boston, MA (US)

(*) Notice: Subject to any disclaimer, the term of this patent is extended or adjusted under 35 U.S.C. 154(b) by 916 days.

(21) Appl. No.: 14/426,424

(22) PCT Filed: Sep. 6, 2013

(86) PCT No.: PCT/US2013/058459
§ 371 (c)(1),
(2) Date: Mar. 6, 2015

(87) PCT Pub. No.: WO2014/039790
PCT Pub. Date: Mar. 13, 2014

(65) Prior Publication Data
US 2015/0216436 A1    Aug. 6, 2015

Related U.S. Application Data

(60) Provisional application No. 61/698,264, filed on Sep. 7, 2012.

(51) Int. Cl.
*A61B 5/04* (2006.01)
*A61B 5/0476* (2006.01)
(Continued)

(52) U.S. Cl.
CPC ........ *A61B 5/0476* (2013.01); *A61B 5/04012* (2013.01); *A61B 5/4094* (2013.01);
(Continued)

(58) Field of Classification Search
CPC .......................... A61B 5/04012; A61B 5/4094
See application file for complete search history.

(56) References Cited

U.S. PATENT DOCUMENTS

2003/0032001 A1* 2/2003 Broderick .......... A61B 5/14542
435/4
2006/0200038 A1* 9/2006 Savit .................... A61B 5/0476
600/544
(Continued)

FOREIGN PATENT DOCUMENTS

WO    WO 2012/021789 A1    2/2012

OTHER PUBLICATIONS

Takahashi et al, Antipsychotics reverse abnormal EEG complexity in drug-naïve schizophrenia: A multiscale entropy analysis, 2010, Neuroimage, 51(1): 173-182.*

(Continued)

*Primary Examiner* — Christian Jang
(74) *Attorney, Agent, or Firm* — Wolf, Greenfield & Sacks, P.C.

(57) ABSTRACT

Methods and apparatus for identifying and using at least one nonlinear feature determined from multiscale electroencephalography (EEG) data to evaluate an epileptogenicity level of a patient is described. A multiscale algorithm is applied to EEG data recorded from the patient to produce scaled EEG data. At least one nonlinear feature value for the received EEG data and/or the scaled EEG data is determined and the at least one nonlinear feature value is used, at least in part, to evaluate the epileptogenicity level of the patient.

17 Claims, 18 Drawing Sheets

(51) Int. Cl.
    *A61B 5/00* (2006.01)
    *G06F 19/00* (2018.01)
(52) U.S. Cl.
    CPC ............ *A61B 5/726* (2013.01); *A61B 5/7264* (2013.01); *A61B 5/7275* (2013.01); *G06F 19/00* (2013.01); *A61B 5/7253* (2013.01)

(56) References Cited

U.S. PATENT DOCUMENTS

2010/0280579 A1* 11/2010 Denison ............ A61N 1/36082
    607/62
2011/0029038 A1* 2/2011 Hyde ................ A61B 5/04001
    607/45

OTHER PUBLICATIONS

Adeli et al, A Wavelet-Chaos Methodology for Analysis of EEGs and EEG Subbands to Detect Seizure and Epilepsy, IEEE Trans Biomed Eng, 54(2): 205-211.*
Kalpakam et al, Haar Wavelet Decomposition of EEG Signal for Ocular Artifact De-Noising: A Mathematical Analysis, 2004, The 2nd Annual IEEE Northeast Workshop on Conference: Circuits and Systems, pp. 141-144.*
Acharya et al, Application of recurrence quantification analysis for the automated identification of epileptic EEG signals, 2011, Int J Neural Syst, 21(3): 199-211.*
Aarabi et al, A rule-based seizure prediction method for focal neocortical epilepsy, 2012, Clinical Neurophysiology, 123(6): 1111-1122.*
Silva et al, Correlation Dimension Maps of EEG from Epileptic Absences, 1999, Brain Topography, 11(3): 201-209.*
Heyden et al, Non-linear analysis of intracranial human EEG in temporal lobe epilepsy, 1999, Clinical Neurophysiology, 110(10): 1726-1740.*
Kang et al, Multiscale Entropy Analysis of EEG for Assessment of Post-Cardiac Arrest Neurological Recovery Under Hypothermia in Rats, 2009, IEEE Trans Biomed Eng, 56(4): 1023-1031.*
International Search Report and Written Opinion dated Nov. 25, 2013 for Application No. PCT/US2013/058459.
International Preliminary Report on Patentability dated Mar. 19, 2015 for Application No. PCT/US2013/058459.
Yun Chen et al., Multiscale recurrence analysis of long-term nonlinear and nonstationary time series, Mar. 26, 2012, pp. 978-987, vol. 45, No. 7, Choas, Solitons and Fractals, Pergamon, Oxford, GB.

* cited by examiner

DETECTION OF EPILEPTOGENIC BRAINS WITH NON-LINEAR ANALYSIS OF ELECTROMAGNETIC SIGNALS

RELATED APPLICATIONS

This Application is a national stage filing under 35 U.S.C. 371 of International Application PCT/US2013/058459, filed Sep. 6, 2013, which claims priority under 35 U.S.C. § 119(e) to U.S. Provisional Patent Application Ser. No. 61/698,264 filed Sep. 7, 2012, the contents of both of which are incorporated herein by reference in their entirety.

BACKGROUND

Epilepsy, one of the most prevalent chronic neurological diseases, affects approximately 0.6-1% of the general population, representing an economic burden of 0.1-1% of the total budget of health care systems in some parts of the world, and a significant proportion of these costs can be attributed to the way in which epilepsy is diagnosed. Epilepsy is characterized by the predisposition to develop spontaneous unprovoked seizures (epileptogenicity). Presently, the diagnosis of epilepsy relies on a patient's clinical history and is based on identifying surrogate markers for epileptogenicity such as the presence of repeated seizures. Seizures are the response of the brain to multiple factors, including internal dynamical tendency or "epileptogenicity level", environmental factors and triggering mechanisms. Seizures can occur in any brain, including apparently normal brains, if the appropriate stimulus is applied. Stimuli that can evoke seizures include hyperventilation, electroshock and photo stimulation. Because of their unpredictable nature, seizures are often difficult to observe while a patient is in the clinic, and this inability to observe seizures in a timely manner often leads to a delay in the diagnosis of patients with epilepsy, which in turn delays treatment for the patient. Clinical events that are suggestive of seizures are confirmed with the concomitant electroencephalogram (EEG) recording that demonstrates their epileptic nature.

One of the most frequent epilepsy syndromes are idiopathic generalized epilepsies, and among them childhood and adolescence absence epilepsy. In these patients, no tangible structural brain abnormality is present on available brain imaging and structural MRI brain images are usually normal or similar to those patients without epilepsy. The diagnosis in absence epilepsy can be easily obtained by recording absence seizures even on routine EEG, therefore confirming the diagnosis by recorded EEG seizures. Additionally, these patients usually do not have any other obvious structural brain changes that can be detected easily with current structural brain imaging techniques. Therefore, this patient population is an ideal group to analyze brain changes related to epilepsy without confounding structural brain changes.

SUMMARY

Conventional methods for diagnosing epilepsy involve several clinical visits and work-up studies, making it time-consuming and very expensive. More importantly, the diagnosis of several seizures only provides an approximation to the diagnosis of epilepsy. As discussed briefly above, epilepsy is the predisposition to spontaneously develop seizures and this predisposition cannot be currently diagnosed by direct methods. That is, epilepsy is the tendency of a given brain to develop seizures, and the occurrence of several epileptic seizures is not more than a rough surrogate marker of this tendency. The inventors have recognized and appreciated that conventional methods for diagnosing epilepsy may be improved by identifying biomarkers for epilepsy by analyzing electric or electromagnetic signals from patients with a propensity of having seizures. To this end, some embodiments, described in more detail below, identify measurable nonlinear features in electric or electromagnetic signals that may be used as reliable biomarkers to diagnose epilepsy without the need to identify the occurrence of repeated seizures.

Mounting evidence suggests that absence seizures are part of a generalized epilepsy spectrum, with overlapping genetic and EEG markers. Other generalized and even focal epilepsies may present with a similar EEG and clinical seizure presentation, possibly indicating that the preliminary results discussed herein may apply to these populations as well and may also represent other cognitive states or identifiers.

Some embodiments have applications related to methods, computer-readable media, and/or computer systems for analysis of electromagnetic data for the detection of reliable biomarkers for epilepsy. For example, some embodiments may be directed to a method of diagnosing a patient as having epilepsy, the method comprising: receiving electroencephalography (EEG) data recorded from the patient; applying, using at least one processor, a multiscale algorithm to the received EEG data to produce scaled EEG data; determining at least one nonlinear feature value for the received EEG data and/or the scaled EEG data; and diagnosing the patient as having epilepsy based, at least in part, on the at least nonlinear feature value.

In some embodiments, the multiscale algorithm is applied by applying a wavelet transform to the received EEG data with scales defined by factors of two. In some embodiments, the wavelet transform uses a Haar basis function or any other wavelet basis function.

In some embodiments, the multiscale algorithm is applied by applying successive averaging of the received EEG data to create the scaled EEG data as a coarse-grained time series.

In some embodiments, determining at least one nonlinear feature value comprises determining an entropy value for the received EEG data and/or the scaled EEG data.

In some embodiments, determining at least one nonlinear feature value comprises determining at least one recurrence quantitative analysis value. In some embodiments, the at least one recurrence quantitative analysis value comprises recurrence rate, determinism, laminarity, or any combination thereof.

In some embodiments, the received EEG data does not include activity related to hyperventilation.

In some embodiments, the method may further comprise recording a time series of EEG data from the patient, wherein the received EEG data is a segment of the recorded time series of EEG data. In some embodiments, the segment of the recorded time series of EEG data is at least ten seconds in duration.

In some embodiments, the method may further comprise normalizing the at least one nonlinear feature value prior to using the at least one nonlinear feature value for diagnosis.

In some embodiments, diagnosing the patient based, at least in part, on the at least one nonlinear feature value comprises using a statistical learning algorithm to determine whether the patient is likely to have epilepsy. In some embodiments, the statistical learning algorithm uses a support vector machine classifier.

In some embodiments, the received EEG data does not include epileptiform activity.

In some embodiments, the at least one nonlinear feature value comprises a set of nonlinear feature values, wherein the set of nonlinear feature values includes at least one nonlinear feature value determined for at least two scales of the scaled EEG data.

In some embodiments, diagnosing the patient based, at least in part, on the at least one nonlinear feature value comprises diagnosing the patient based, at least in part, on the set of nonlinear feature values.

In some embodiments, the received EEG data comprises EEG data from a plurality of channels, and wherein determining the at least one nonlinear feature value comprises determining the at least one nonlinear feature value for each of the plurality of EEG channels of the received EEG data.

In some embodiments, the received EEG data comprises EEG data from a plurality of channels, and wherein determining the at least one nonlinear feature value comprises determining the at least one nonlinear feature value for a subset of the plurality of EEG channels of the received EEG data. In some embodiments, the subset of the plurality of EEG channels includes a single EEG channel. In some embodiments, the subset of the plurality of EEG channels includes less than all of the plurality of EEG channels.

In some embodiments, the method further comprises generating at least one scalp map, wherein the at least one scalp map is generated based, at least in part, on the at least one nonlinear feature value.

Some embodiments are directed to a computer-readable medium, encoded with a plurality of instructions that, when executed by a computer, performs a method of diagnosing a patient as having epilepsy, the method comprising: receiving electroencephalography (EEG) data recorded from the patient; applying a multiscale algorithm to the received EEG data to produce scaled EEG data; determining at least one nonlinear feature value for the received EEG data and/or the scaled EEG data; and diagnosing the patient as having epilepsy based, at least in part, on the at least nonlinear feature value.

Some embodiments are directed to a computer, comprising: at least one processor programmed to: receive electroencephalography (EEG) data recorded from a patient; apply a multiscale algorithm to the received EEG data to produce scaled EEG data; determine at least one nonlinear feature value for the received EEG data and/or the scaled EEG data; and determine whether the patient has epilepsy based, at least in part, on the at least nonlinear feature value.

Some embodiments are directed to a method of identifying a set of nonlinear features useful for evaluating an epileptogenicity level of a patient, the method comprising: receiving first EEG data from patients with epilepsy and second EEG data from patients without epilepsy; generating, using at least one processor, first multiscaled EEG data from the first EEG data and second multiscaled EEG data from the second EEG data; determining first nonlinear feature values for the first multiscaled EEG data and second nonlinear feature values for the second multiscaled EEG data; and determining the set of nonlinear features based, at least in part on a comparison of the first nonlinear feature values and the second nonlinear feature values.

In some embodiments, the set of nonlinear features includes a single nonlinear feature. In some embodiments, the single nonlinear feature is determined for multiple scales of the corresponding first and second multiscaled EEG data.

In some embodiments, the set of nonlinear features comprises at least two nonlinear features, and wherein each of the at least two nonlinear features are determined for multiple scales of the corresponding first and second multiscaled EEG data.

In some embodiments, determining the set of nonlinear features based, at least in part on a comparison of the first nonlinear feature values and the second nonlinear feature values comprises performing a cross-validation computation by applying a statistical learning algorithm to the first nonlinear feature values and the second nonlinear feature values. In some embodiments, the statistical learning algorithm uses a support vector machine classifier. In some embodiments, the cross-validation computation is performed for combinations of two, three, or four nonlinear feature values, on each scale of the first and second multiscale EEG data.

In some embodiments, determining the set of nonlinear features based, at least in part on a comparison of the first nonlinear feature values and the second nonlinear feature values comprises determining which combination of nonlinear feature values demonstrate the highest sensitivity in distinguishing the first EEG data and the second EEG data.

In some embodiments, determining first nonlinear feature values for the first multiscaled EEG data and second nonlinear feature values for the second multiscaled EEG data comprises determining the first nonlinear feature values and the second nonlinear feature values corresponding to at least one recurrence quantitative analysis value.

In some embodiments, the method further comprises recording the first EEG data from the patients with epilepsy and the second EEG data from the patients without epilepsy, wherein the first EEG data and the second EEG data does not include epileptiform activity.

In some embodiments, the first EEG data and the second EEG data, each include EEG data recorded from a plurality of EEG channels, and the method further comprises: determining a subset of the plurality of EEG channels exhibiting significant differences in at least one nonlinear feature value between the first EEG data and the second EEG data. In some embodiments, the method further comprises generating at least one scalp map identifying the subset of the plurality of EEG channels.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
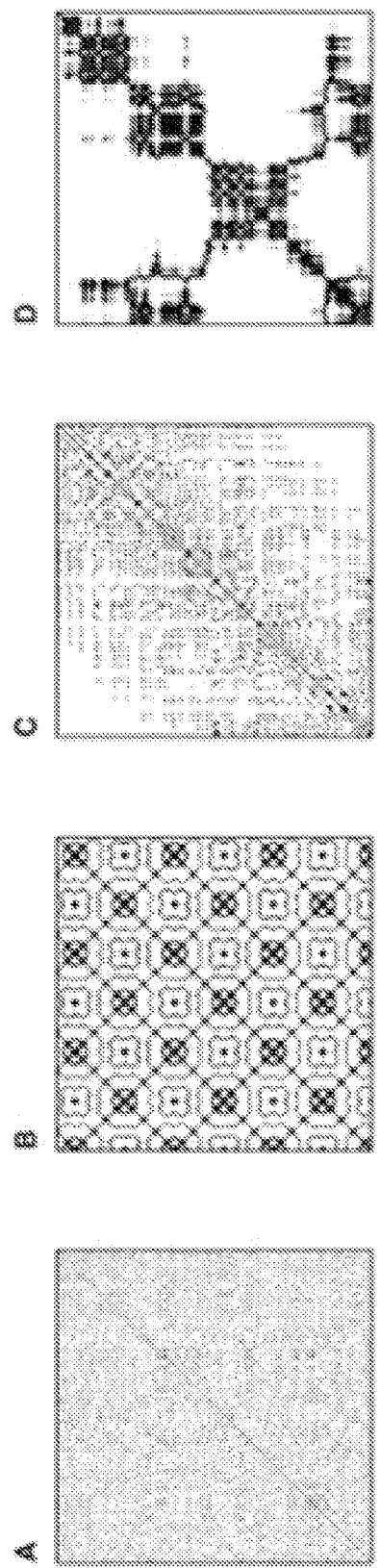
FIGS. 1A-D illustrate characteristic typologies of recurrence plots for different time series signals in accordance with some embodiments.

Following below are more detailed descriptions of various concepts related to, and inventive embodiments of, methods and apparatus according to the present disclosure for determining reliable biomarkers for epilepsy. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

As discussed above, the pathological condition identified as epilepsy is the predisposition of a given brain to have seizures during normal activities that do not evoke seizures in most people. As there are not direct biomarkers of this predisposition, the diagnosis of epilepsy relies on the detection of repeated seizures. However, due to the paroxysmal and unpredictable presentation of epileptic seizures, recording a seizure while the patient is in the clinic is frequently difficult. Changes in the neuronal network may also occur prior to seizure onset and are difficult to detect. Earlier detection may open a window for prevention of possible seizures, treatment of epileptogenesis, and prevention of neurocognitive deficits that are frequently seen in patients with epilepsy and epileptic encephalopathies.

The concept of 'epileptogenicity level' suggests that every brain is potentially subject to a seizure. Normal brains have a low level of epileptogenicity, while people who have regular, unprovoked seizures might be said to have a high epileptogenicity level. If the brain is considered to be a complex dynamical system, then it is reasonable to expect that a physical and thus measurable aspect of brain dynamics may be identified with the epileptogenicity level. A potential biomarker for epilepsy might then be found in a set of parameters that characterize the various complex system dynamics.

Some embodiments are directed to identifying biomarkers for epilepsy and epileptiform activity beyond recorded seizures and inter-ictal epileptiform discharges. Such embodiments use complex systems analysis of EEG signals to detect the emergence of epileptic brain function and monitor the developmental trajectory of the disorder in patients with benign focal epilepsy and childhood absence epilepsy. In particular, it is envisioned that some embodiments could be used as a much sought after and needed biomarker for early detection of childhood epilepsy and monitoring its developmental trajectory with no additional need to capture random seizures or spikes and sharp waves in the EEG signal.

The method and apparatus described herein may be broadly applicable for detecting the emergence of epileptogenicity before the onset of overt seizures in both idiopathic and symptomatic cases, such as following traumatic brain injury or infectious insults in young children and provide an opportunity to explore interventions that aim to screen for propensity of having seizures, treat epileptogenesis early, prevent seizures, and detect and diagnose epilepsy without recording inter-ictal epileptiform discharges or seizures.

Previous efforts to identify biomarkers for epilepsy have focused primarily on the ability to detect seizures prior to their onset. For example, various measures of nonlinear dynamics have been computed from EEG time series in order to detect changes immediately prior to the onset of seizures or epileptiform discharges. Permutation entropy was found to change significantly up to five seconds before seizure onset in rat models of absence epilepsy. Kolmogorov entropy, Correlation Dimension, Relative Wavelet Energy and Approximate Entropy have all demonstrated some success for detecting pre-seizure onset periods, but could not distinguish healthy controls from epilepsy patients during seizure-free periods. Mixed results have been reported for automated seizure detection algorithms based on four different measures (principal eigenvalue, total power, Komogorov entropy, correlation dimension). The algorithms were found to be patient-age specific and no one algorithm performed well on all patients.

Rather than focusing on identifying biomarkers to detect seizures, few studies have attempted to assess biomarkers for the overall propensity to have seizures (i.e., epileptogenicity). Some embodiments described herein are directed at identifying a set of nonlinear dynamical measures from EEG data that facilitate the diagnosis of epilepsy. In particular, some embodiments are directed to performing Recurrence Quantitative Analysis (RQA) of EEG signals at multiple scales.

Recurrence plots were originally introduced in the late 1980's to graphically represent the dynamics of complex systems. The subsequent emergence of computers as a general tool for computational experimentation with chaotic systems enabled the development of RQA, a statistical approach to the dynamically informative patterns that arise in recurrence plots. RQA is a useful tool analyzing real-world, noisy, high dimensional data. RQA is a general empirical approach and incorporates nonlinear measures such as entropy and generalized synchronization and is in principle able to characterize all the essential dynamics of a complex system. An example of typical recurrence plots for several different time series is shown in FIG. 1. FIGS. 1A-D illustrate characteristic typology of recurrence plots for (A) uniformly distributed noise, (B) periodic time series, (C) drift (logistic map corrupted with a linearly increasing term) and (D) disrupted (Brownian motion). Analysis of the patterns in recurrence plots yields RQA values that characterize nonlinear dynamical systems. The dynamics of each EEG recording are revealed by a unique pattern in the recurrence plot, yielding distinct quantitative RQA values. If epileptogenicity corresponds to an actual dynamical state in the brain, then RQA measures may be capable of detecting systematic changes in the brain that signal the development of a propensity to seizures and inter-ictal epileptiform discharges.

A single measure of system complexity that can be computed from physiological time series is sample entropy. Although entropy measures have been used to characterize time signals for more than sixty years, the computation of entropy on multiple scales derived from a time series was only introduced recently. Multiscale entropy measures have been shown to be useful for detecting changes in physiological systems, including mental disorders such as Alzheimer's Disease, schizophrenia, the effect of antipsychotic drugs, normal aging, and autism.

An exemplary multiscale algorithm was described by Costa et al. (e.g., see Costa et al., *Physical Review*, 2005, 71 (2 Pt 1), pp. 021906, the entirety of which is incorporated by reference herein). This algorithm involves two steps. The first step is a coarse-graining procedure that uses successive averaging of a time series to create new coarse-grained time series. For a window size t, t=1, 2, . . . j, the $j^{th}$ coarse-grain series, $y^t_j$, is computed by averaging non-overlapping windows:

$$y_j^\tau = \frac{1}{\tau} \sum_{i=(j-1)\tau+1}^{j\tau} x_i,$$

where $x_i$ is the original time series of length N and t is the scale factor satisfying 1<t<N/t.

Alternatively, the first step may be accomplished by applying a wavelet transform using a Haar basis function with scales defined by factors of two: 1, 2, 4, 8, and so on. The second step in the multiscale algorithm of Costa et al. is to compute the sample entropy for each scaled time series derived from the original time series. In some embodiments, described in more detail below, the multiscale concept was extended for the first time to recurrence plot analysis by performing RQA on multiple scales derived from the originally recorded EEG signals.

Figure 2:
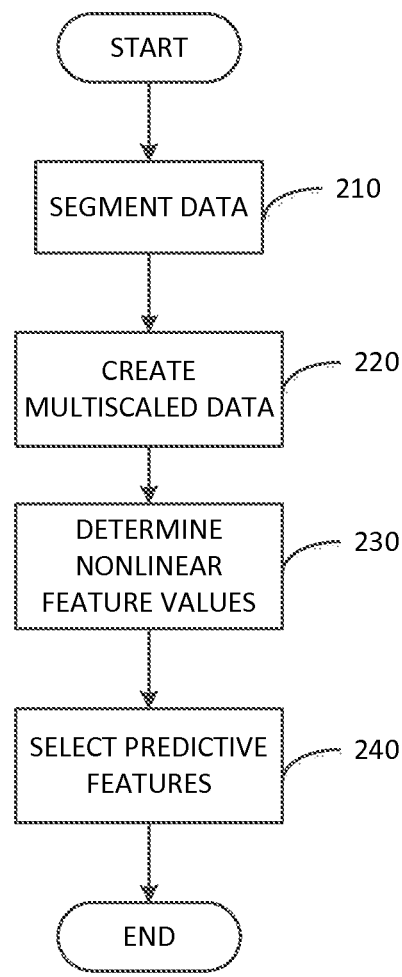
FIG. 2 illustrates a flow chart for an exemplary process for identifying nonlinear features useful for diagnosing epilepsy in accordance with some embodiments.
Figure 3:
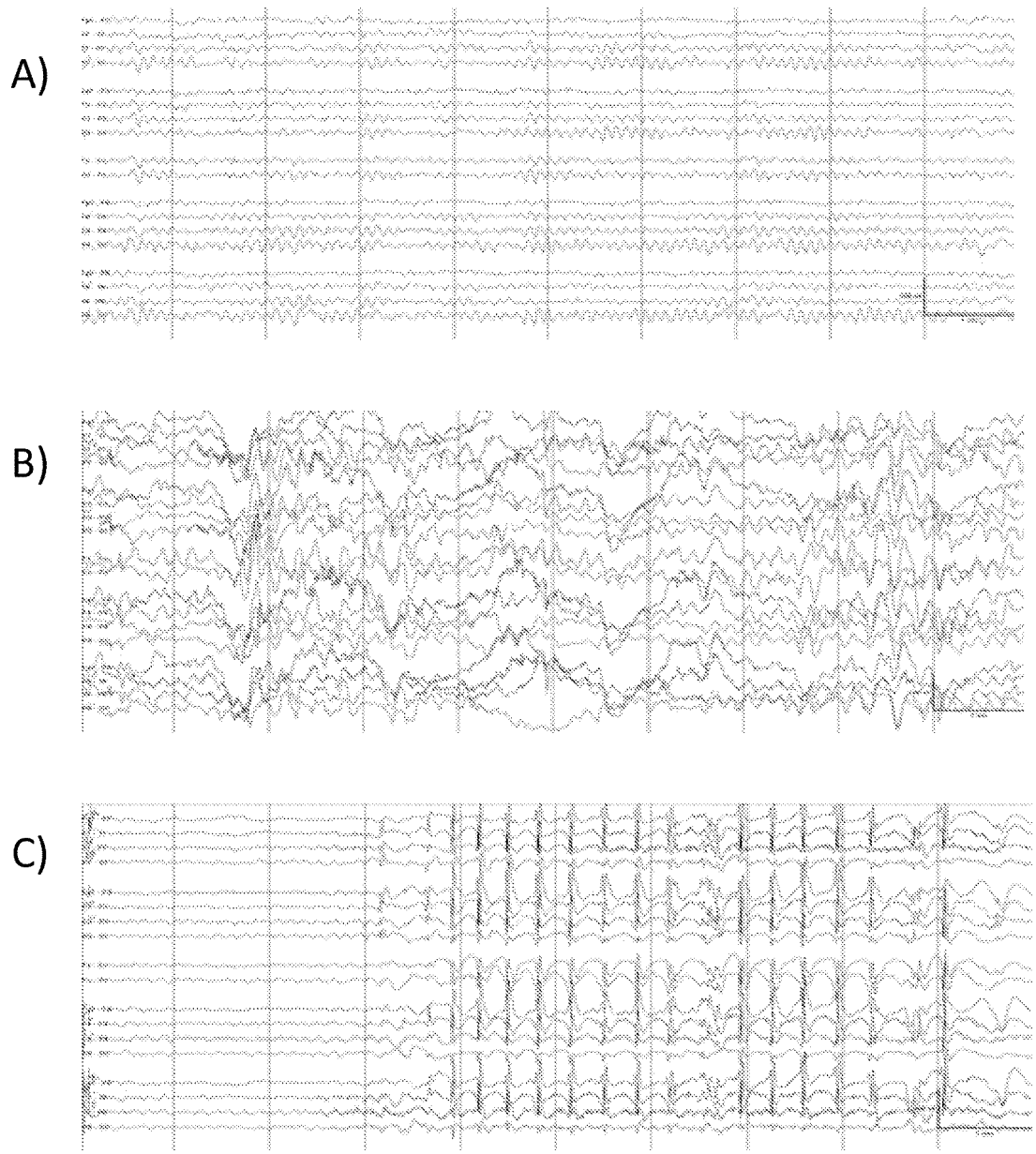
FIGS. 3A-C illustrate exemplary EEG data recorded during (A) baseline, (B) patient hyperventilation, and (C) epileptiform activity, used in accordance with some embodiments.

FIG. 2 illustrates an exemplary process for analyzing EEG data to identify nonlinear features from EEG data in accordance with some embodiments. In act 210, EEG data is segmented to identify EEG segments having different characteristics. FIG. 3 illustrates an example of segmented data that may be used in accordance with some embodiments. FIG. 3A illustrates EEG segments during baseline without spikes, FIG. 3B illustrates EEG segments during patient hyperventilation without spikes, and FIG. 3C illustrates EEG segments during a run of generalized spike-waves. The EEG data may be segmented in any suitable way and the segments may be of any suitable length. In one implementation described in more detail below, the EEG data was segmented into ten-second segments.

After the EEG data is segmented, the process proceeds to act 320, where a multiscale algorithm is applied to each of the segmented time series. Any suitable number of scales may be generated from the original EEG recording. For example, in the illustrative implementation discussed in more detail below, five scaled time series (i.e., the original time series and four additional time series derived from the original time series) were used.

The process then proceeds to act 230, where one or more nonlinear feature values are determined from the multiscaled segmented data. Any number of nonlinear feature values (e.g., entropy and RQA values) may be determined in act 230 and embodiments are not limited based on which or how many nonlinear feature values are employed in a particular implementation. After determining the nonlinear feature value(s), the process proceeds to act 240, where one or more of the features are selected as being predictive of epilepsy. The one or more features may be selected in any suitable way including, but not limited to, ranking the features according to significant differences between epileptic and control groups, as discussed in more detail below. In some embodiments, prior to feature selection, the features may be normalized over the set of all subjects and scales for each nonlinear value.

In one implementation described in more detail below, to assess the ability of the selected features to accurately characterize individual patients as having epilepsy, the selected features were subjected to a validation procedure using a statistical learning algorithm. Cross validation accuracy calculations were then performed for combinations of nonlinear values, on each scale, on a chosen subset of most significant channels and the subset of features with the highest sensitivity and/or specificity was selected as the predictor for identifying patients with epilepsy.

An exemplary implementation in accordance with embodiments is now described. In this implementation, a database of patients with an electroencephalogram (EEG) was analyzed and two populations of subjects were identified: patients with typical absence seizures (absence cases) and patients that underwent an EEG for different reasons but were eventually determined to not have epilepsy (controls). All subjects met the following inclusion criteria: 1) age between 1 month and 21 years, and 2) normal neuropsychological development. In addition, cases had several episodes of electro-clinically documented absence seizures. The diagnosis of typical absence seizures was determined after careful evaluation of the clinical and EEG features by at least one board-certified clinical neurophysiologist. Controls met the following criteria: 1) at least one EEG study because of the clinical suspicion of seizures, 2) normal EEG study, and 3) very low-risk of a diagnosis of epilepsy after a thorough electro-clinical evaluation. Causes for performing an EEG study in controls included daydreaming, syncope, night terrors or sleepwalking. The main demographic features of cases and controls are summarized in Table 1. Twenty-four absence cases and twenty-six controls were used in this exemplary implementation.

TABLE 1

Demographical and clinical features of the population of patients.

| Parameter | Absence Cases N = 24 | Control N = 26 |
|---|---|---|
| Age at performance of the EEG study (years) | 8.95 ± 2.07 | 8.4 ± 6 |
| Gender (male/female) | 67%/33% | 20%/80% |

Figure 4:
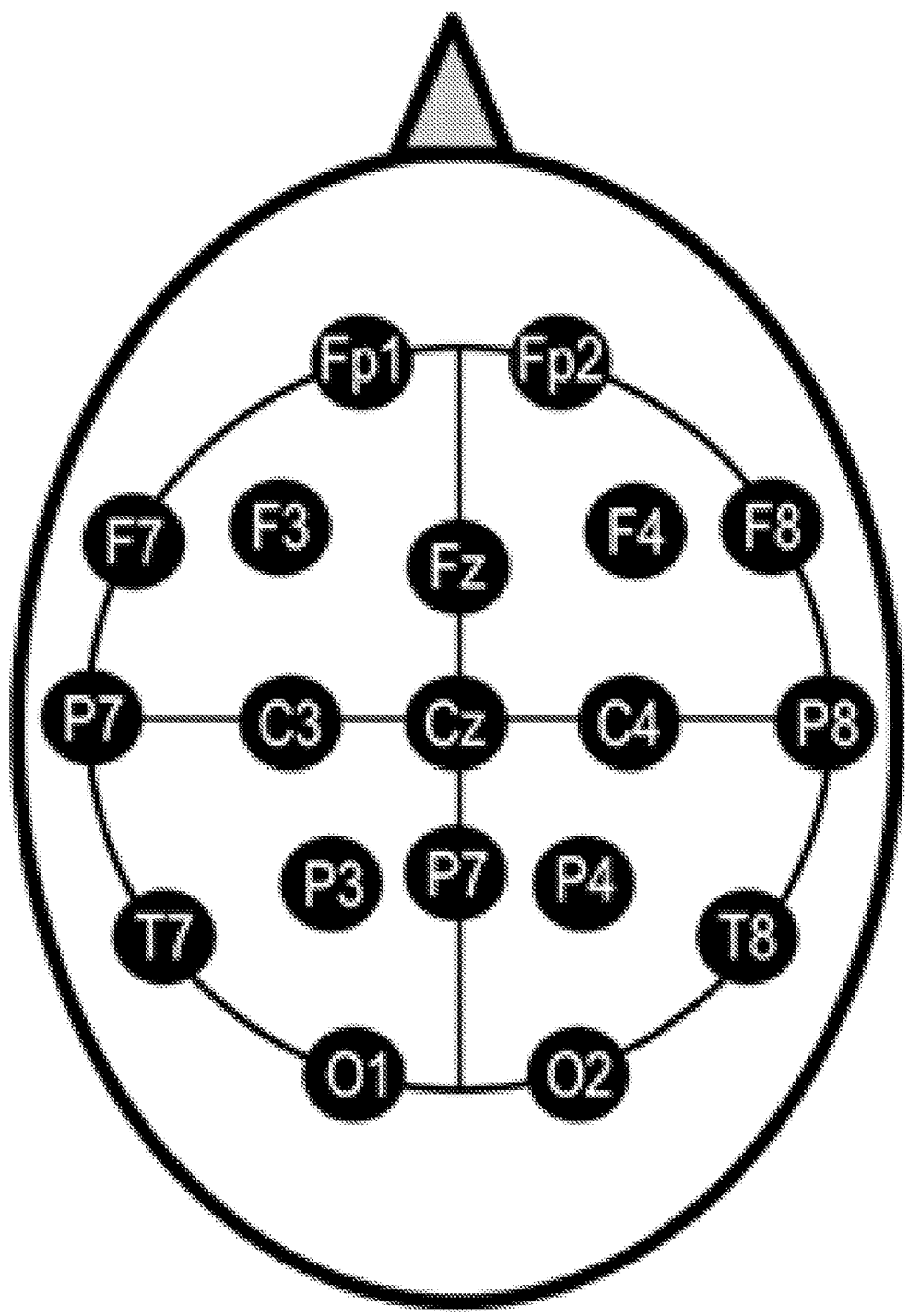
FIG. 4 is a schematic illustrating electrode placement used to record EEG data in accordance with some embodiments.

EEG segments of 10-30 seconds duration each were identified and collected. In cases three segments were collected: baseline without spikes (FIG. 3A), hyperventilation without spikes (FIG. 3B), and spikes (FIG. 3C). In controls, two segments were collected: baseline without spikes, and hyperventilation without spikes. These samples were saved as European Data Format (EDF) files. For each subject, segments of equal length were collected on 19 channels located according to the standard 10-20 system, as shown in FIG. 4. In this implementation, only the absence cases without apparent spikes were used.

Each of the EEG time series was processed in an identical manner in the following steps. Ten second segments (2000 points) were selected from EEG data for each patient. Further analysis revealed that using 20 second segments did not change the RQA or sample entropy values appreciably. At least half of the chosen segments for epilepsy patients were examined and only segments that were free of spike and wave activity were chosen for classification into either absence cases or controls.

After segmentation of the EEG data, a multiscale algorithm was applied to each of the time series to create four new time series in addition to the original. The additional time series created using multiscale analysis are referred to herein as 'scales.' A Haar wavelet transform was applied to each original signal to produce the four new time series. Alternatively, the multiscale coarse-grain procedure described by Costa et al., or any other suitable multiscale algorithm may be used. In this implementation, only powers of 2 coarse-grain scales: $1=2^0$ (the original signal), $2=2^1$, $4=2^2$, $8=2^3$, $16=2^4$ were used, although it should be appreciated that any number of scales may be used and embodiments are not limited in this respect. The original and derived time series are designated herein by the terms scale 0, scale 1, scale 2, scale 3 and scale 4.

For each of the five scales derived from each EEG sensor, sample entropy was computed using known algorithms (e.g., see Zhang et al., 2009) along with nineteen RQA values (e.g., see Marwan et al., 2007c). Thus, in this implementation. 95 (5*19) time series were derived for each subject using the multiscaling process. Twenty nonlinear values were computed for each of these time series, yielding a total of 1900 dynamical features for each subject, which include multiscale entropy and multiscale RQA values. The total set of values computed for each patient constitutes the feature set for that patient.

In this implementation, prior to feature selection, all features were normalized to the range [0, 1] over the set of all subjects and scales for each nonlinear variable. For example, for sample entropy the range and minimum were computed over all sample entropy values for all subjects and all scales and used to normalize all sample entropy values.

When the number of features for classification far exceeds the number of samples in the sample population, a well-known phenomenon, sometimes called the 'curse of dimensionality', results in a very sparse distribution of points in the feature space and poor performance by learning algorithms. Accordingly, to reduce the dimensionality of the classification problem, rather than using all of the features for classification, a subset of the features were selected.

Feature selection to extract the most useful features from high-dimensional data is a challenging problem and an area of active research in biostatistics and machine learning in general. Recent studies have shown that a simple feature ranking approach based on the student's t-test is an effective way to select features. Accordingly, in this implementation, a simple univariate student's t-test was used to rank the features to determine which features to use for classification. However, it should be appreciated that any method of feature selection including, but not limited to, complex wrapper, and embedded methods may alternatively be used.

Figure 5:
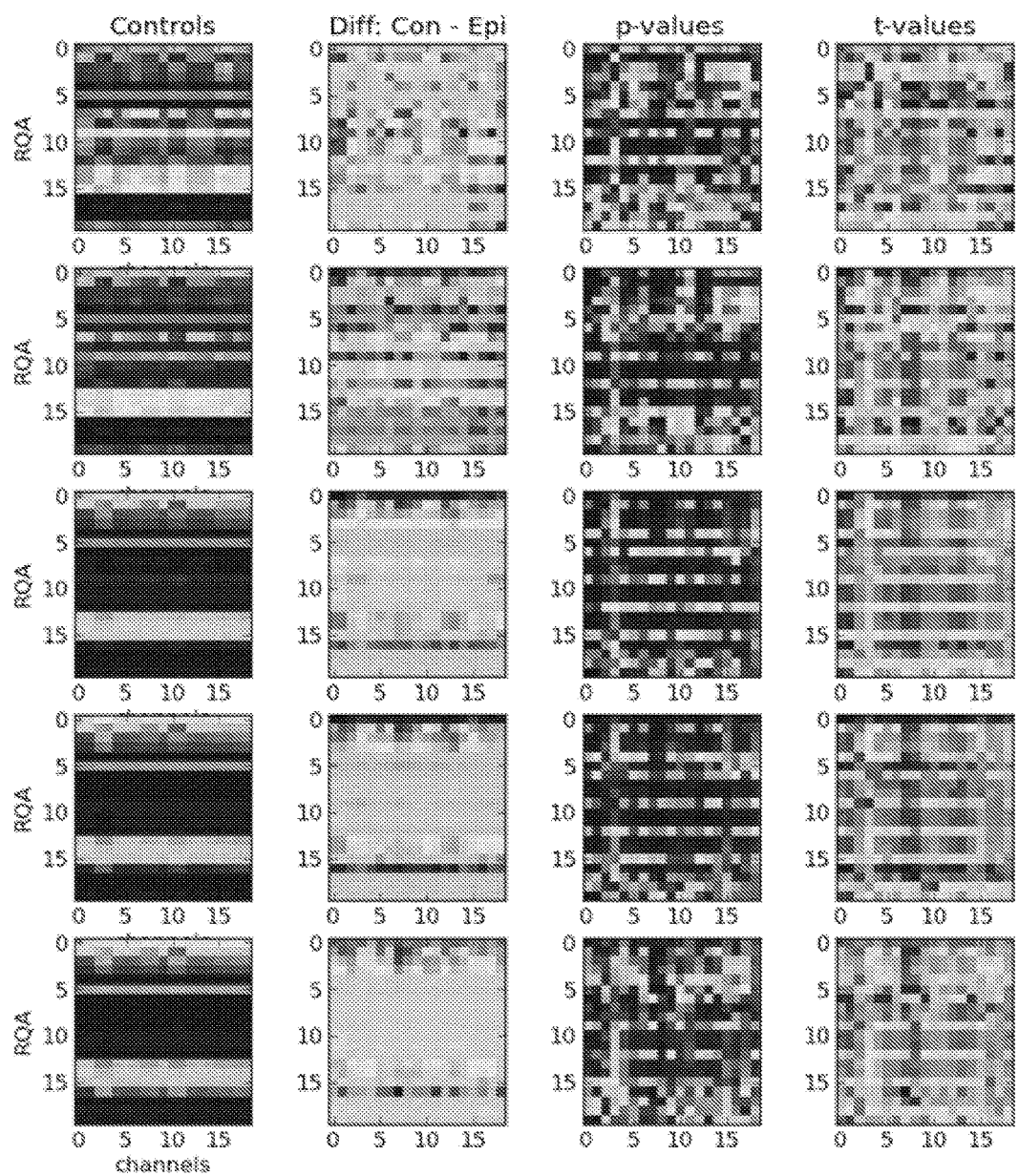
FIG. 5 illustrates ranking matrices for a plurality of nonlinear feature values determined in accordance with some embodiments.

In this implementation, the first step in feature ranking was to compute p-values using a student's t-test for each feature to determine features that were most significantly different between the absence cases and control groups. A color-coded ranking matrix is shown in FIG. 5. The leftmost column of FIG. 5 illustrates normalized values for every nonlinear feature used. The column second from the left of FIG. 5 illustrates group mean differences for the different nonlinear features. In p-value matrices (third column of FIG. 5), the color range is 0 to 0.05. All points in the matrix having p-values of 0.05 or greater and may be considered to be not significantly different, when considered alone, between the two groups. Other colors can be used to identify features that are significantly different between the groups. Horizontal axes on each plot of FIG. 5 are channel numbers. Vertical axes correspond to nonlinear features including sample entropy, RR, DET, LAM, DET/RR, LAM/DET, W_prob, L_max, V_max, W_max, L_mean, TT, L_entr, V_entr, W_entr, T1, F_min, and T2. This information can also be displayed as scalp plots showing the spatial distribution of each of the feature values and how they differ between groups.

After computing p-values for all features, the features were ordered starting with the lowest score (most significant). The first 100 most significant features were examined to determine which sensor locations were most common and which nonlinear features were most common. It was found that all of the 100 most common features were from sensors C3, C4, F7, F8, P3 and P4, with C4 and P4 being less common than the other four sensors. In a similar manner, the nonlinear measures that were most common in the most significant features were: recurrence rate (RR), determinism (DET), the ratio DET/RR, maximum diagonal line length (L_max) and laminarity (LAM). Several other measures also appeared, though less commonly: Vertical line maximum length (V_max), sample entropy (SampE), and the entropy of the diagonal line lengths (L_entr). The physical meaning of these variables, and in particular their meaning in the context of time series dynamics is an area of active research, and will not be discussed further. Significant features appeared in all scales from 0 to 4, but were most common in scales 1, 2 and 3, thereby demonstrating that multiscaling in combination with RQA algorithms may be a source of important information for detecting the presence of epilepsy or a heightened epileptogenicity level.

In this implementation, it was not assumed that the univariate significance of each feature would necessarily correlate with the effects of combining features in the classification process. That is, less significant features may together be highly significantly different between the two groups and thus be necessary for classification. Though classification strategies tend to be data-specific, one rule of thumb that has been effective is to have more than ten times as many subjects as features or predictors. If the ratio of subjects to features is smaller, it is possible that dimensionality effects may degrade the performance of the classifier. Since the population in this example consisted of only 50 subjects, ideally not more than 5 features should be used for classification. However, it should be appreciated that in some embodiments, more or less features may be used for classification and embodiments are not limited in this respect. For example, combinations for two or more non-linear values, on more than one scale, at several scalp locations may be needed to detect the presence of epilepsy.

In this implementation, after ranking the features, as discussed above, the most significant sensors together with one, two, three or four nonlinear values on one scale (for example, RR on scale 1, DET on scale 0 each represent a single value) were exhaustively searched in a 10-fold cross validation calculation to determine a classification accuracy. In this way, the initial ranking information was used to reduce the set of all combinations of features to test for classification efficacy.

Figure 6:
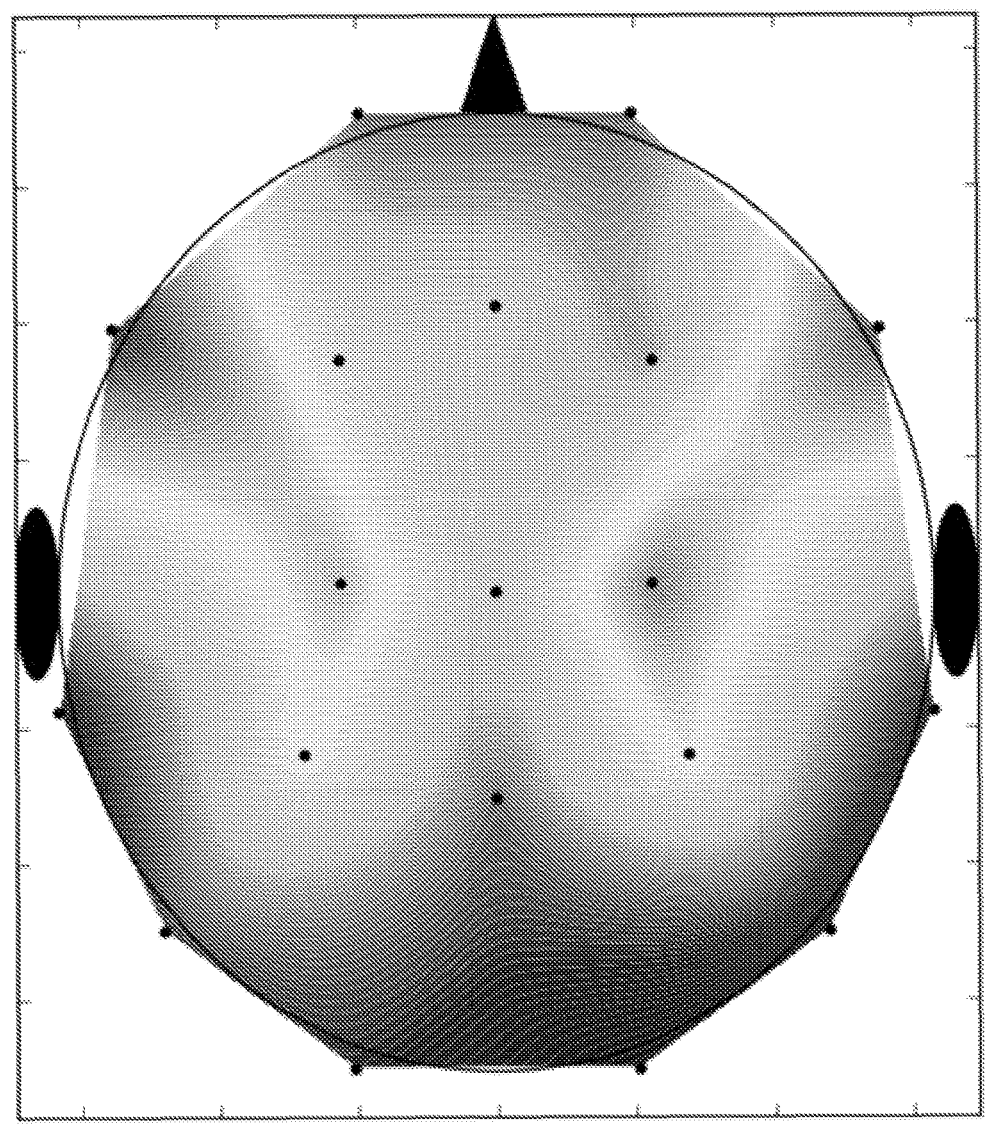
FIG. 6 illustrates a scalp plot showing the EEG channels exhibiting the greatest differences in nonlinear feature values between control and epilepsy groups determined in accordance with some embodiments.
Figure 7:
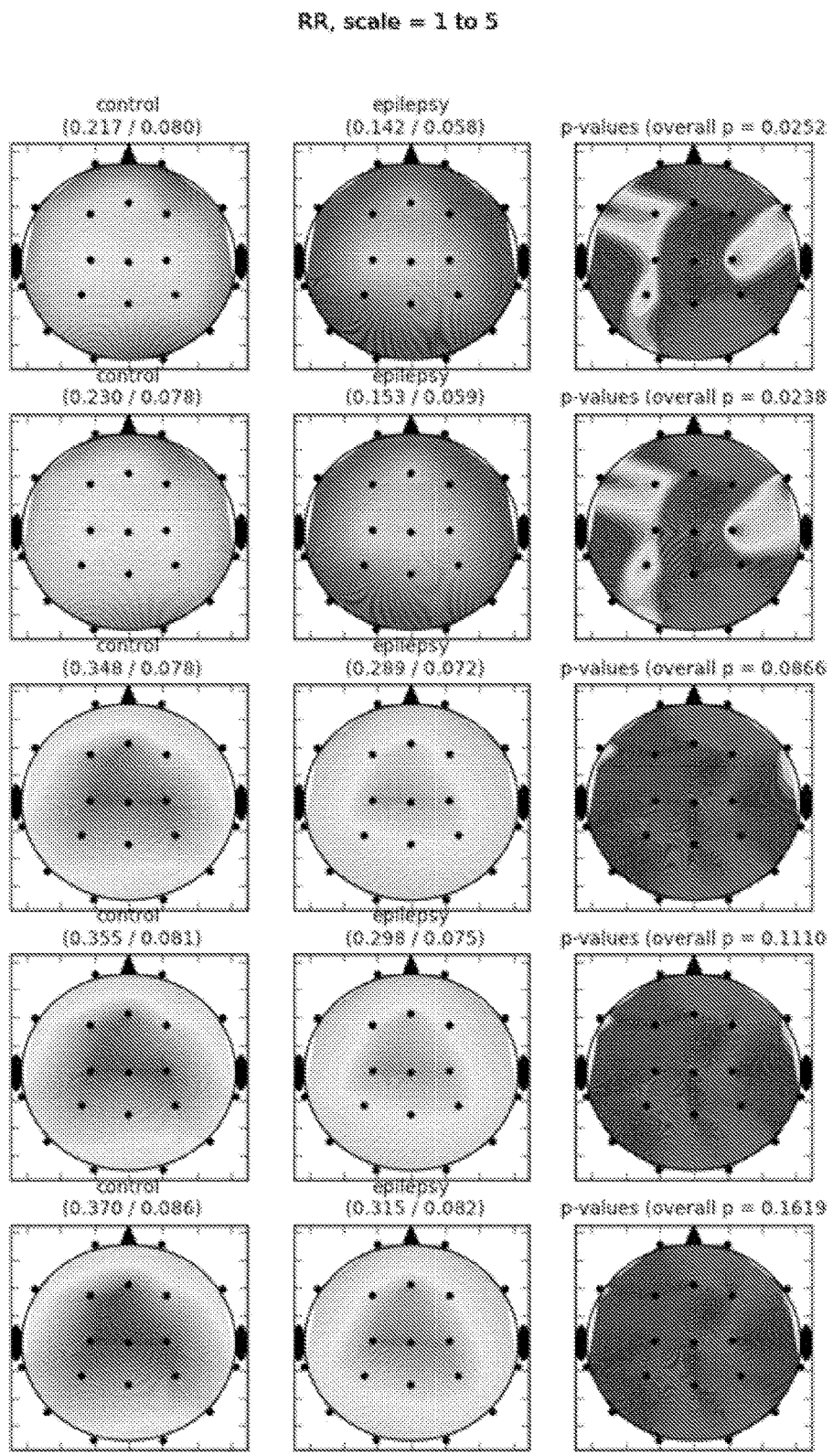
FIG. 7 illustrates scalp plot maps for the recurrence rate (RR) nonlinear feature using multiscale data determined in accordance with some embodiments.
Figure 8:
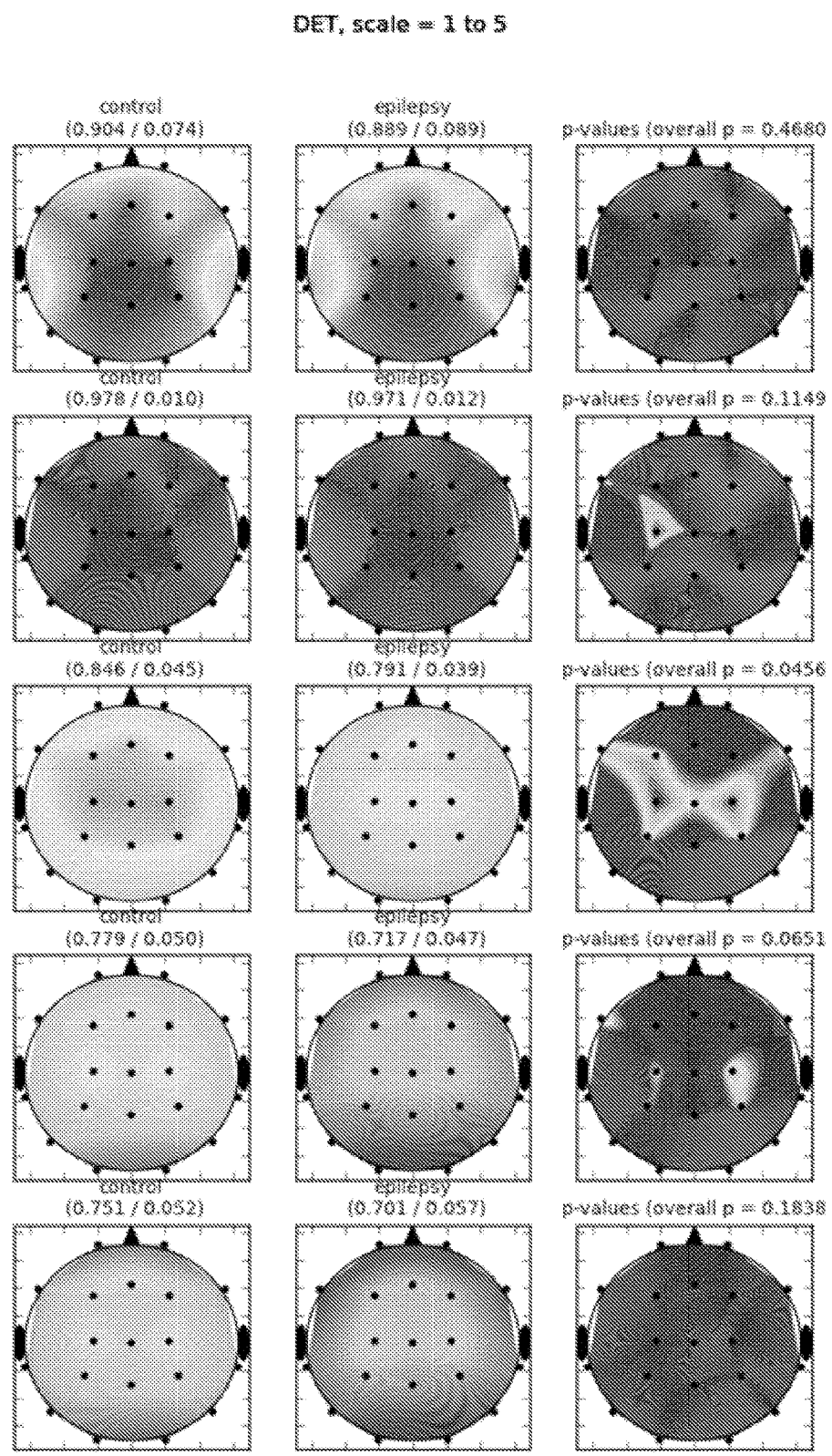
FIG. 8 illustrates scalp plot maps for the determinism (DET) nonlinear feature using multiscale data determined in accordance with some embodiments.
Figure 9:
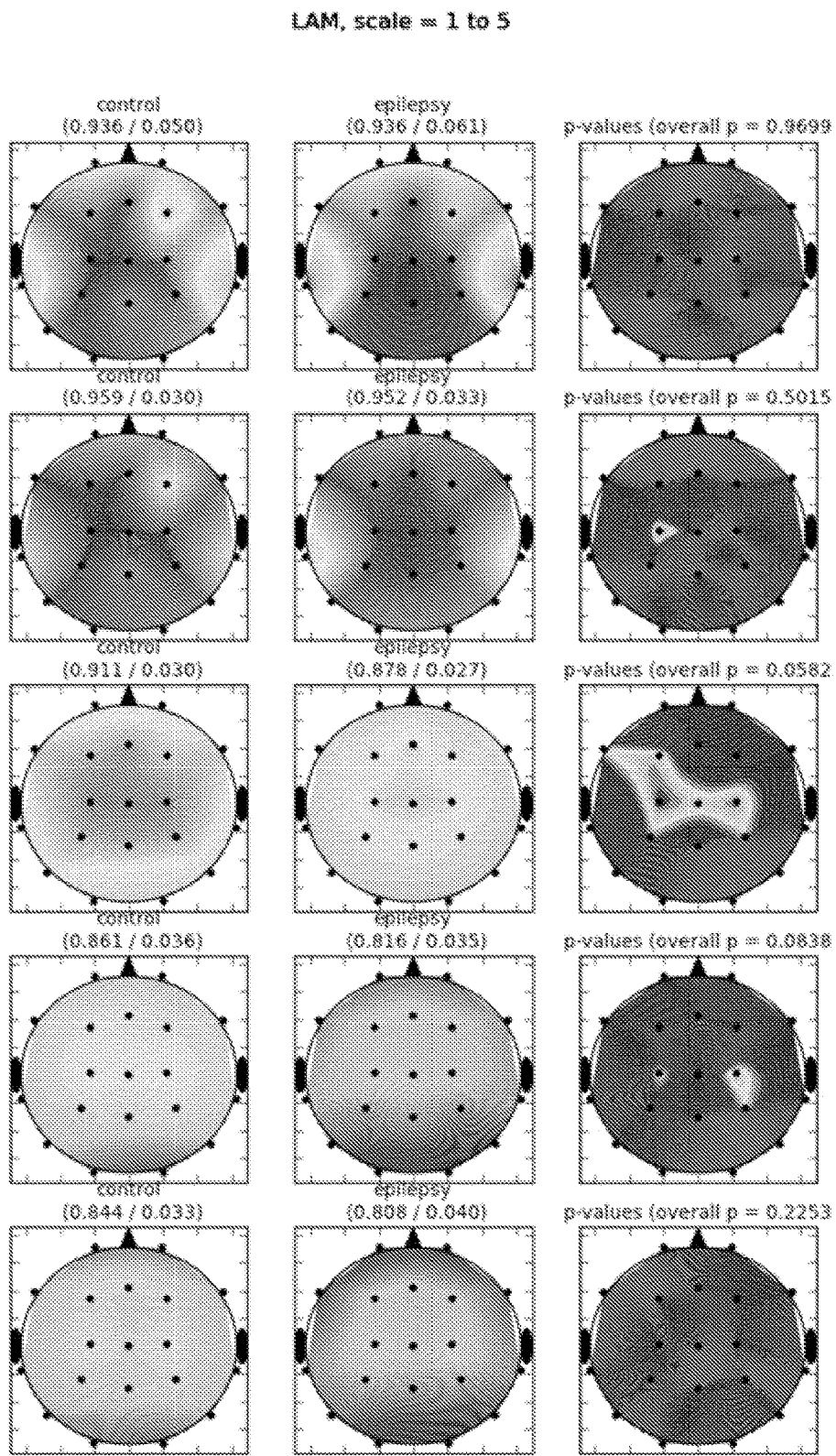
FIG. 9 illustrates scalp plot maps for the laminarity (LAM) nonlinear feature using multiscale data determined in accordance with some embodiments.
Figure 10:
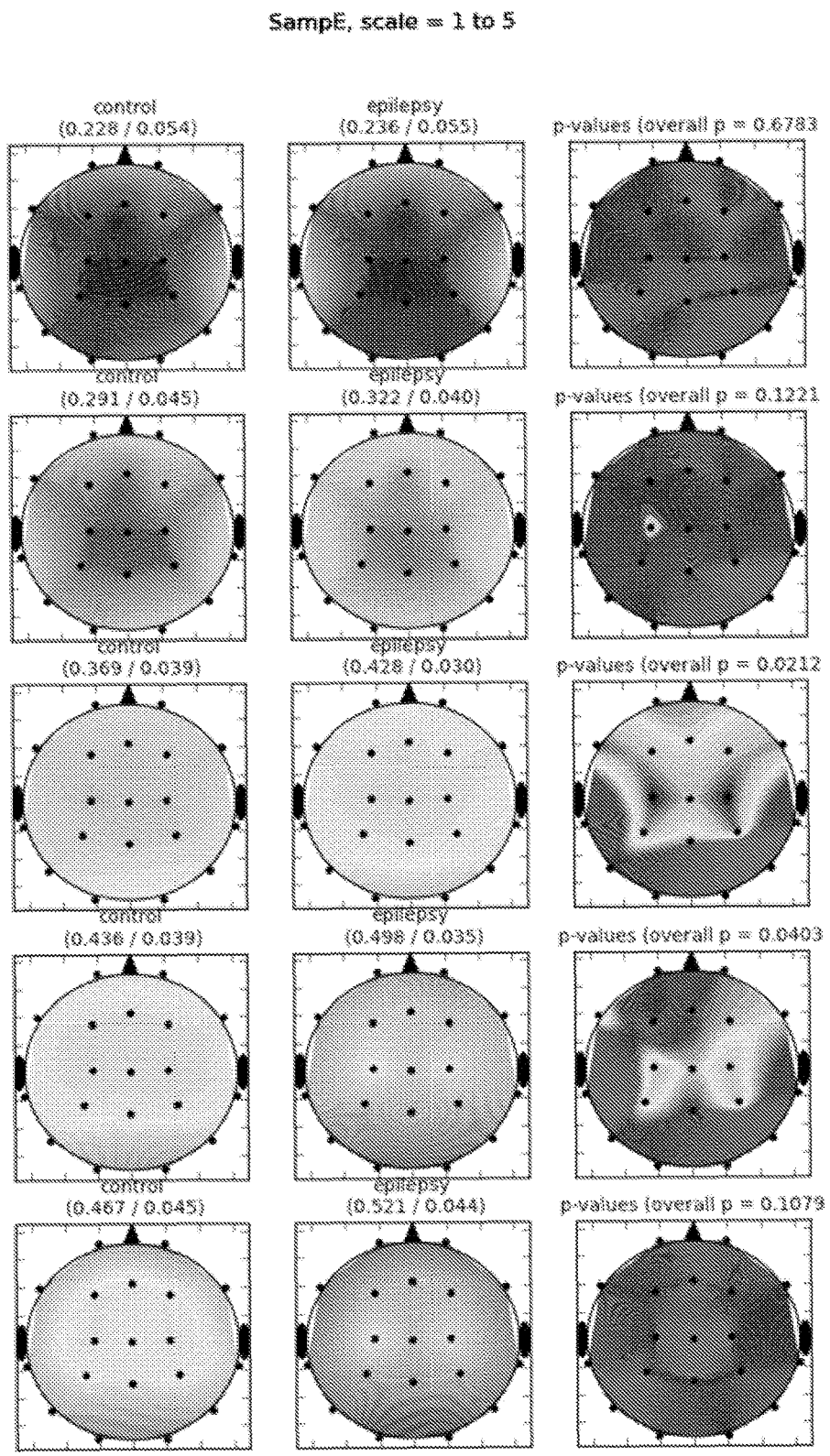
FIG. 10 illustrates scalp plot maps for the sample entropy (SampE) nonlinear feature using multiscale data determined in accordance with some embodiments.
Figure 11:
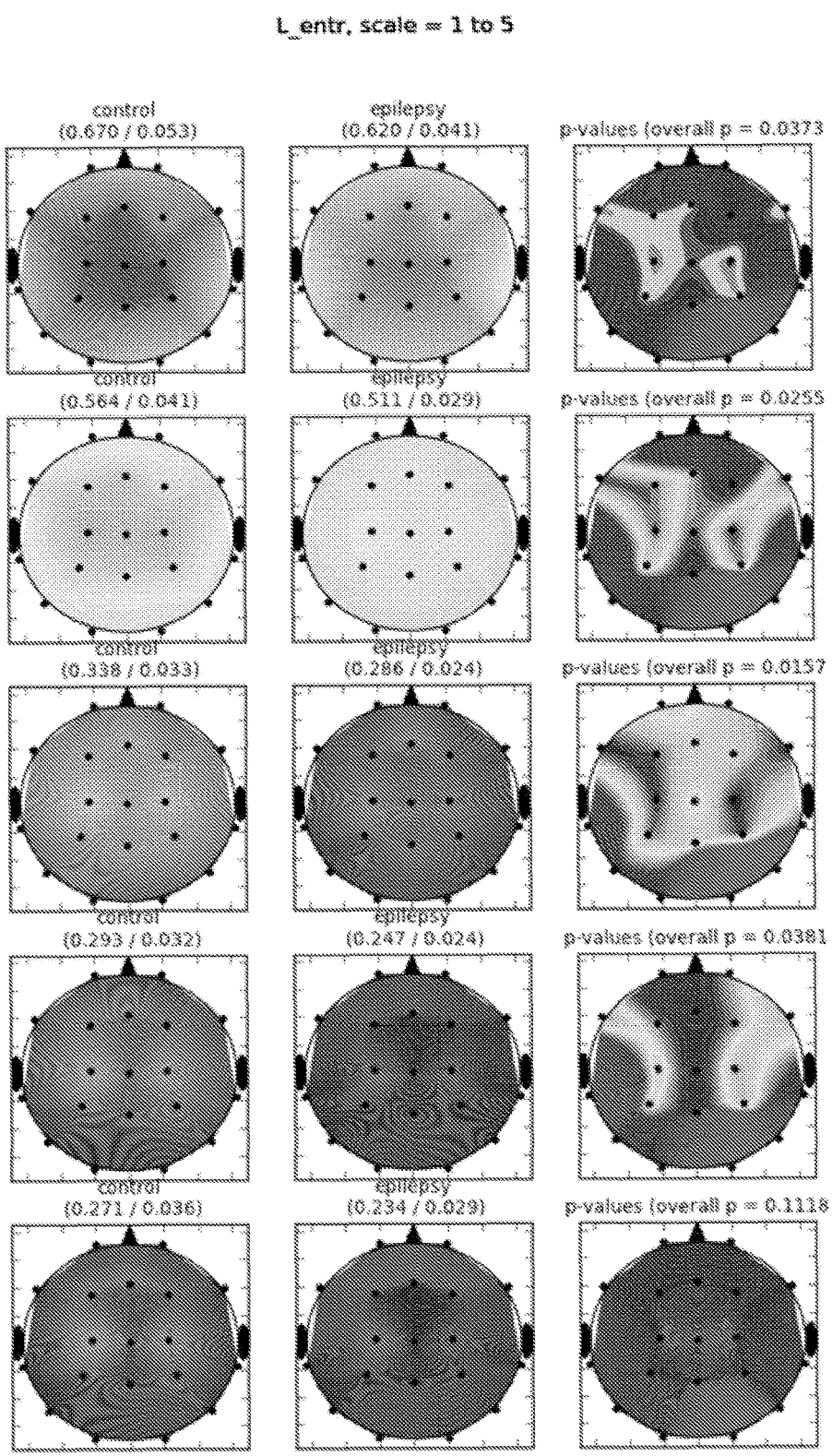
FIG. 11 illustrates scalp plot maps for the line length entropy (L_entr) nonlinear feature using multiscale data determined in accordance with some embodiments.

Preliminary results produced by applying the methods in accordance with the described implementation above, are discussed in more detail below. As described above, the significance of group differences for each of the features, a t-test was used to compute p-values for each feature. All features were ranked by p-value. Of the 100 most significant features, all were in locations C3, C4, F7, F8, P3 or P4, with scales 0 to 3 represented, but 2 and 3 most common. The most common nonlinear measures in the top 100 most significant features list included sample entropy (SampE), recurrence rate (RR), determinism (DET), laminarity (LAM), maximum line length (L_max), trapping time (TT), line length entropy (L_entr). The most significant nonlinear measures can be identified as horizontal lines in the p-value column of FIG. 5. This information was used for feature selection. Table 2 contains actual frequency numbers for features and channel locations from all features with p<0.05 from the total of 1900 features. FIG. 6 illustrates a scalp plot showing the significant channels visually.

TABLE 2

Frequency of occurrence of significant (p < 0.05) feature values on all scales at sensor locations.

| Chan | F7 | F8 | C3 | C4 | P3 | P4 | F3 | Fz | Cz | F4 | Pz | Fp1 | Fp2 | P7 | O1 | T8 | T7 | P8 | O2 |
|---|---|---|---|---|---|---|---|---|---|---|---|---|---|---|---|---|---|---|---|
| Sig # | 50 | 46 | 37 | 42 | 32 | 33 | 26 | 23 | 19 | 16 | 12 | 12 | 12 | 9 | 7 | 4 | 3 | 1 | 0 |

In this implementation, classification and cross validation calculations were performed with a statistical learning algorithm using the Orange Data Mining package (see, e.g., Curk et al., 2005), using the python scripting interface. Other classification and cross validation algorithms may alternatively be used and embodiments are not limited in this respect. The support vector machine (SVM) classifier is an implementation of the libSVM package that is widely used for machine learning in bioinformatics and many other fields. The automatic SVM parameter tuning method was used, which uses radial basis functions (RBF) by default and implements an internal cross validation for parameter tuning. For this implementation, the SVM algorithm was chosen because it tends to give better results than many other approaches. In particular, the SVM algorithm takes into account the effect of linear combinations of input features. However, other classifiers known to those of skill in the art including, but not limited to, k-nearest neighbors, naïve Bayesian classifiers and decision trees may alternatively be used.

The significance of the classification results was estimated empirically using the permutation approach described in Golland and Fischl, 2003. This method essentially randomly shuffles the classification labels and computes the accuracy for each of the learning algorithms using a 10-fold cross validation. By computing many cross validations with randomly permuted labels, an estimate of how well the learning algorithm can classify the subjects with nonsense labels can be obtained.

Epileptiform activity is frequently observed in frontal and occipital regions in absence epilepsy. The most significant regions displayed in FIG. 6 do not represent the sites of epileptic activity. Rather, these are the locations where absence patients and controls exhibit the greatest number of significant nonlinear value differences during inter-ictal periods when no epileptiform activity is present.

The most commonly occurring nonlinear measures were also tabulated numerically. The number of each significant measure over all channels and scales is shown in Table 3. This information was also used for feature selection. Together, the most common channels and nonlinear measures were used as input to a classification algorithm and searches were performed over subsets of these to find those that gave the best predictive accuracy.

TABLE 3

Frequency of occurrence of most common significant (p < 0.05) nonlinear features.

| Nonlinear Value | TT | L_mean | L_entr | L_max | SampE | RR | DET | LAM |
|---|---|---|---|---|---|---|---|---|
| Significant Occurrences | 51 | 48 | 41 | 27 | 27 | 24 | 20 | 13 |

Figure 12:
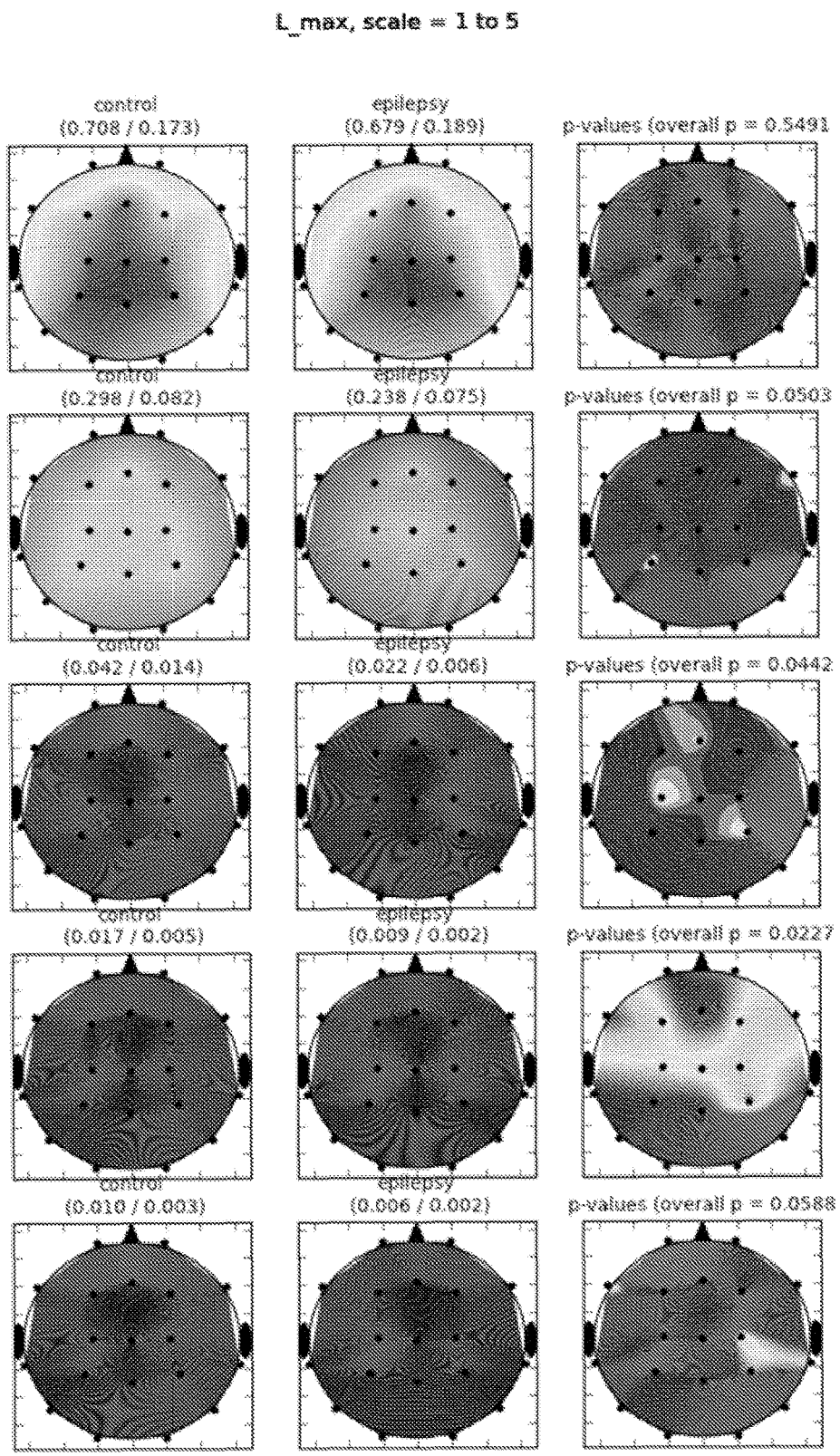
FIG. 12 illustrates scalp plot maps for the maximum line length (L_max) nonlinear feature using multiscale data determined in accordance with some embodiments.

FIGS. 7-12 show scalp plots for four of the nonlinear values that were found to be most significantly different between absence cases and controls from a univariate perspective, that were also found to be the most useful for prediction in the cross validation study discussed below. These include RR (FIG. 7), DET (FIG. 8), LAM (FIG. 9), SampE (FIG. 10), L_entr (FIG. 11) and L_max (FIG. 12). Rows correspond to scales 0 to 4, with 0 defining the original EEG signal. The three columns from left to right in each of FIGS. 7-12 correspond to mean values over all controls, mean over all absence cases, and the p-values for group differences, respectively. The color schemes in columns 1 and 2 of each of FIGS. 7-12 are scaled from 0.0 to 1.0, as all values are normalized to this scale. p-values are shown on a color scale from 0.0 to 0.05. Thus, red represents all p-values higher than 0.05 at that location. This enables significantly different sensors to be seen visually.

Significant group differences in a number of the nonlinear measures were observed, with clear spatial distribution patterns and clear differences across scales. In these preliminary data, the most significant group differences did not appear in values derived from the original signal, but in scales 1, 2 and 3, in certain channels and nonlinear values. This result indicates that the nonlinear features contain information that is significantly different in the absence epilepsy cases, even during non-spiking inter-ictal periods. Using this information, a cross validation study was performed to determine if these differences would enable individuals to be classified as having absence epilepsy or not.

Group differences in univariate measures do not reveal relationships among several variables (whether different scales, sensor locations or nonlinear measures) that may define classification boundaries between groups. Because the number of study subjects in this initial investigation was small (i.e., 50), it is desirable to choose only a few of the 1900 features as inputs to a classification algorithm to avoid the sparse distribution of examples that results from curse of dimensionality as discussed previously. The univariate significance was used to make a first choice. However, many of the single variables might be highly correlated, so the best subset of features for classification was not be determined on that basis alone.

An exhaustive search was done using the features listed in Table 3, selecting one, two, three or four features, on each scale. That is, RR on scale 0, RR(0), and RR(2) were considered two different, independent values for cross validation and prediction. Several sets of sensors were used: [F7, F8], [F7, F8, C4, P3], [F7, F8, C3, C4, P3, P4, F3, Fz] and [all sensors]. For each sensor, one, two, three or four nonlinear values on a single scale (0 through 4) were chosen and a 10-fold cross validation accuracy was computed. Thus, 2 to 8 features were used for prediction with the first set of two channels, 4 to 32 features for the second set of 4 channels, and so on. The goal was to find the combination of sensor locations and nonlinear features that gave the most accurate classification of absence cases. Since the sample set was relatively small, the smallest possible feature set was desired. However, results were also compared to larger sets of features.

When only one nonlinear feature was used, predictive accuracy was less than 80% for all sets of channels. This indicated that no single nonlinear value, on any scale, is sufficient for the most accurate classification of the two groups (absence versus controls).

Similarly, when two nonlinear values were used with each of the sets of channel locations, only two or three combinations of features gave predictive accuracies greater than 80%. Both of these required values on two different scales and involved combinations of RR and DET. The most combinations of nonlinear values that gave predictive accuracies above 80% were obtained by using 3 values, regardless of the number of channels. With four nonlinear values per channel, the predictive accuracy did not increase. These results are summarized in Table 4.

In this illustrative example, different features from at least two different scales were required to attain 80% or higher accuracy. This suggests that multiscale nonlinear features contain information that distinguishes absence epilepsy cases from controls and that nonlinear features (e.g., sample entropy and RQA values) derived from the original EEG signals alone may not be sufficient to accurately distinguish absence epilepsy from controls. The most common nonlinear features to give predictive accuracies above 80% are combinations of RR, DET and LAM, with the others much less common. However, these are not the features with the three highest univariate significance, as shown in Table 3. The most accurate predictions were obtained by using four channels, as shown in Table 4, with the nonlinear features RR(3), DET(3), L_max(0) and SampE(0).

TABLE 4

Summary of exhaustive search for highest accuracy predictions using subsets of the most significant nonlinear features on four subsets of channels, over all scales.

| Highest accuracy | Number of channels | Most common features | # combinations that yield acc >80% |
|---|---|---|---|
| 0.84 | 2<br>F7, F8 | RR, DET, LAM, TT | 11 |
| 0.86 | 4<br>F7, F8, C4, P3 | RR, DET, LAM | 19 |
| 0.82 | 8<br>F7, F8, C3, C4, P3, P4, F3, Fz | RR, DET, LAM | 20 |
| 0.80 | 19<br>all channels | RR, DET, LAM | 4 |

The significance of the classification accuracy was assessed empirically using the permutation strategy described in Golland and Fischl. If the class labels are randomly permutated, a new classification accuracy can be computed using 10-fold cross validation, to serve as a baseline. In this implementation, 100 random permutations were performed with a 10-fold cross validation for each machine classification calculation. The p-value was determined by counting the number of random classifications for which the accuracy was equal to or higher than the accuracy for the true labels. A summary of the results reported in this section is shown in Table 5.

TABLE 5

Classification of epilepsy cases using SVM algorithm and various combinations of features as input.

| Channels | Best Nonlinear Measures (scale) | Acc | Sens | Spec | AUC | IS | Brier | pvalue |
|---|---|---|---|---|---|---|---|---|
| F7, F8 | LAM (0), DET (1), L_mean (2) | 0.840 | 0.846 | 0.833 | 0.817 | 0.269 | 0.360 | 0.00 |
| F7, F8, C4, P3 | SE(0), SE(1), DET(2) | 0.860 | 0.846 | 0.833 | 0.917 | 0.370 | 0.296 | 0.00 |
| F7, F8, C4, P3, C3, P4, Fz, F3 | RR(3), LAM(2), LAM(3) | 0.820 | 0.769 | 0.875 | 0.850 | 0.288 | 0.375 | 0.00 |
| All | RR(1), DET(3) LAM(0) | 0.800 | 0.769 | 0.833 | 0.850 | 0.344 | 0.328 | 0.00 |

Abbreviations used: Acc = accuracy, Sens = sensitivity, Spec = specificity, AUC = area under (ROC) curve, IS=, Brier = brier value, pvalue = empirically-computed p-value.

Hyperventilation is a physiologic state in which there is a higher risk of epileptogenicity. During hyperventilation both absence cases and controls may have a high epileptogenicity and, therefore, they can be difficult to differentiate. In order to control for this possible confounding factor, a subgroup analysis was performed that compared the controls during normal resting state to the same controls during hyperventilation. The goal was to determine if the "artificial" epileptogenicity created by hyperventilation could be detected by the nonlinear analysis described above.

Figure 13:
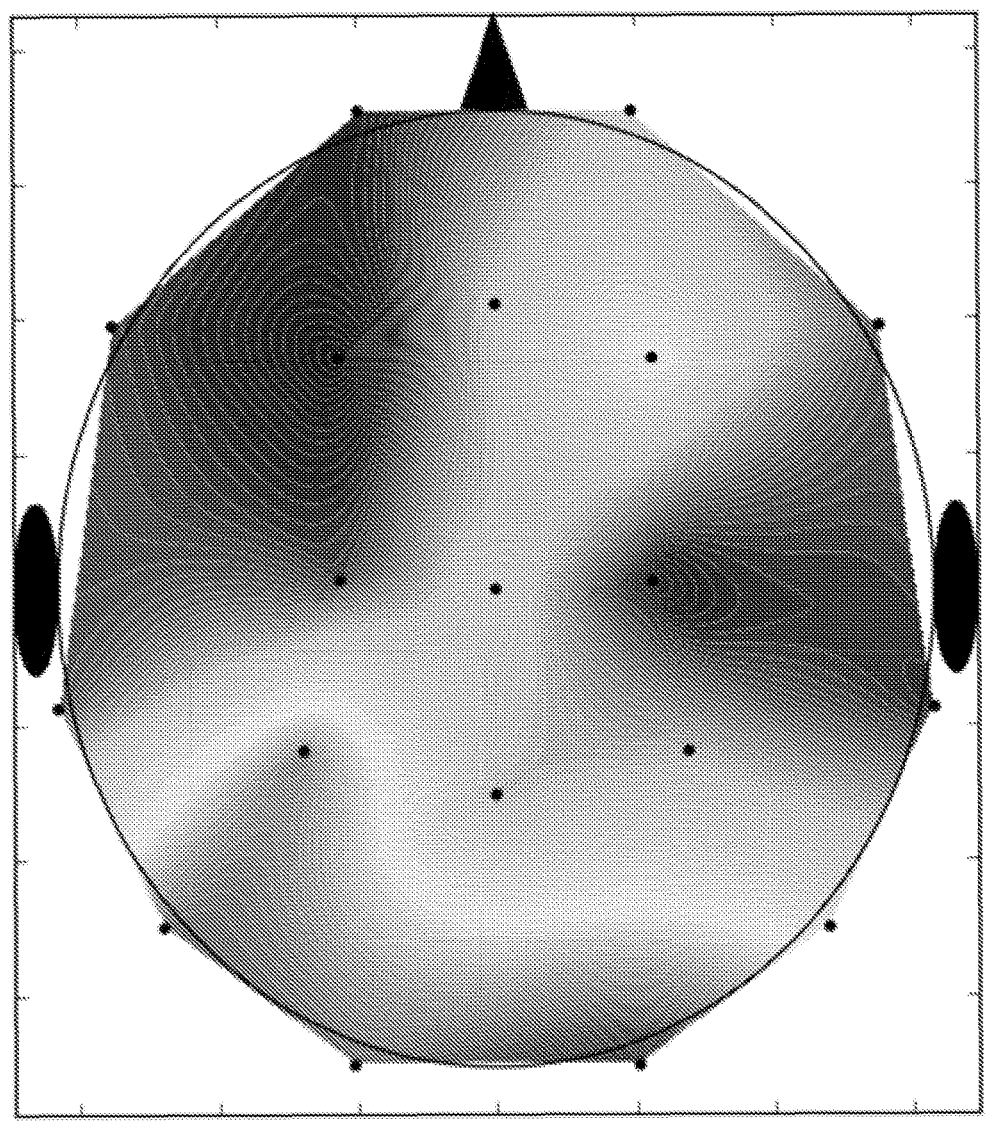
FIG. 13 illustrates a scalp distribution map showing locations where the greatest number of nonlinear features differed in normal control and hyperventilating control subjects.

First, univariate analysis of the most frequent significant channels, shown in FIG. 13, revealed a different pattern than for absence patients. The most frequent significant channels were found in the occipital region. However, the actual numbers were more uniformly distributed over the entire scalp, as shown in Table 6.

TABLE 6

Frequency of occurrence of significant ($p < 0.05$) feature values on all scales at sensor locations.

| Channel | O2 | O1 | P7 | P3 | F4 | P8 | P4 | Cz | Fp2 | Fz | Pz | T7 | F8 | F7 | C3 | Fp1 | T8 | C4 | F3 |
|---|---|---|---|---|---|---|---|---|---|---|---|---|---|---|---|---|---|---|---|
| Sig # | 43 | 39 | 39 | 38 | 33 | 31 | 25 | 28 | 27 | 26 | 25 | 21 | 21 | 20 | 20 | 18 | 19 | 17 | 15 |

The most common nonlinear features that were significantly different between hyperventilating and normal controls included the same set as for the absence cases: SampE, L_entr, DET, RR, LAM and L_max. A similar exhaustive search as described for absence cases was performed. Predictive accuracies were higher, for many more combinations of the nonlinear variables. Results are summarized in Table 7.

TABLE 7

Classification of hyperventilation controls from non-hyperventilating controls using SVM algorithm and various combinations of features as input.

| Channels | Best Nonlinear Measures (scale) | Acc | Sens | Spec | AUC | IS | Brier | pvalue |
|---|---|---|---|---|---|---|---|---|
| F7, F8 | RR (0), L_entr (1), L_entr (2) | 0.967 | 0.909 | 1.000 | 0.950 | 0.504 | 0.195 | 0.00 |
| F7, F8, C4, P3 | SE(0), SE(1), DET(2) | 0.950 | 0.846 | 0.833 | 0.917 | 0.370 | 0.296 | 0.00 |
| F7, F8, C4, P3, C3, P4, Fz, F3 | RR(0), L_max(0), SampE(3) | 0.950 | 1.000 | 0.909 | 1.000 | 0.633 | 0.159 | 0.00 |
| All | RR(0), DET(3) LAM(3) | 0.950 | 1.000 | 0.909 | 1.000 | 0.613 | 0.179 | 0.00 |

In some embodiments, a broad set of nonlinear measures, including sample entropy and/or RQA values, are used to analyze EEG data across multiple scales. Statistical feature selection is used to identify significant values and sensor locations to define input sets to machine learning algorithms. It was hypothesized that non-linear analysis of the signals in the EEG can diagnose epilepsy with a high sensitivity and specificity when compared to the gold-standard diagnosis (clinical history, physical exam and EEG interpreted by the epileptologist).

In the above-described example, patients with absence epilepsy were selected because they represent a common diagnosis in the epilepsy population, are relatively easy to characterize clinically and electroencephalographically, and constitute one of the most homogeneous groups of patients with epilepsy. However, it should be appreciated that EEG data recorded from patients with a propensity to develop other types of epilepsy may also be used and embodiments are not limited in this respect. Additionally, the particular manner in which the data are recorded is not a limiting aspect of embodiments, as any suitable recording techniques may be used.

As described above, the preliminary results demonstrated using an exemplary implementation demonstrate that nonlinear values computed from multiscale EEG signals are significantly different in absence patients during non-spiking inter-ictal periods when compared to non-epileptic controls. A spatial distribution of the frequency of significantly different nonlinear features reveals a pattern that includes sensors in the fronto-central region. When features from these locations were used for classification in an SVM algorithm, classification accuracies of up to 86% can be obtained. The ability of the algorithm to use additional information may be enhanced with larger datasets. The nonlinear values that appear to have the most information for classification are RR, DET, and LAM. However, it should be appreciated that any nonlinear features may be used for classification and these features may differ depending on the patient population being studied. By, computing these values on multiple scales, the predictions were more accurate, as no combinations of up to four features on any set of sensor locations gave accurate classification results if only scale 0 (i.e., the original signal).

Classification of controls and hyperventilating controls with these same variables was highly accurate, implying that these nonlinear values may be sensitive to a general 'epileptogenicity level'. When comparing controls and hyperventilating controls, the significant differences appeared to be more uniformly distributed across the scalp electrodes. Thus, similar classification accuracies of 95% are attained with all combinations of electrodes tested.

It is expected that different epilepsies will reveal different spatial distributions of most frequent significant nonlinear values, but that a similar set of nonlinear values (e.g., RR, DET, and LAM), across multiple scales, will be most likely to detect differences between epilepsy cases and controls.

The preliminary results, described in detail above, were validated in another implementation using larger samples of patients. In this implementation, a database of patients with an electroencephalogram (EEG) was analyzed and two populations of subjects were identified: patients with typical absence seizures (absence cases) and patients that underwent an EEG for different reasons but were eventually determined to not have epilepsy (controls). All subjects met the following inclusion criteria: 1) normal neuropsychological development and 2) no other EEG abnormalities than those consistent with generalized absence epilepsy. Diagnosis was confirmed by documented generalized absence seizures on EEG, and the diagnosis of typical absence seizures was confirmed after careful evaluation of the clinical and EEG features by at least one board-certified clinical neurophysiologist. Controls met the following criteria: 1) at least one EEG study because of the clinical suspicion of seizures, 2) normal EEG study, and 3) very low-risk of a diagnosis of epilepsy after a thorough electro-clinical evaluation. Causes for performing an EEG study in controls included daydreaming, syncope, night terrors or sleepwalking. The main demographic features of cases and controls are summarized in Table 8. Forty absence cases and forty controls were used in this exemplary implementation.

TABLE 8

Demographical and clinical features of the population of patients.

| Parameter | Absence Cases N = 40 | Control N = 40 |
|---|---|---|
| Age at performance of the EEG study (years) | 8.95 ± 2.07 | 8.4 ± 6 |
| Gender (male/female) | 67%/33% | 20%/80% |

In this implementation, sample EEG segments of up to thirty seconds duration were collected from both absence cases and controls. EEG data was sampled at 200 Hz for all subjects. From the absence cases, thirty second samples containing no spikes or evidence of epileptiform activity were selected by an experienced neurologist on visual review. Similarly, thirty second segments were selected from controls after visual review. All EEG samples were awake samples that were normal on visual analysis. These samples were saved as European Data Format (EDF) files. For all subjects, segments of equal length were collected on 19 channels located according to the standard 10-20 system, as described above in connection with FIG. 4. Average referencing was used for all subjects.

Each of the EEG samples was processed in the following steps. Thirty second segments (6000 points) were selected from EEG data for each subject. Only segments that were free of spike and wave activity were chosen for classification. Average referencing was used for all EEG time series.

Figure 15:
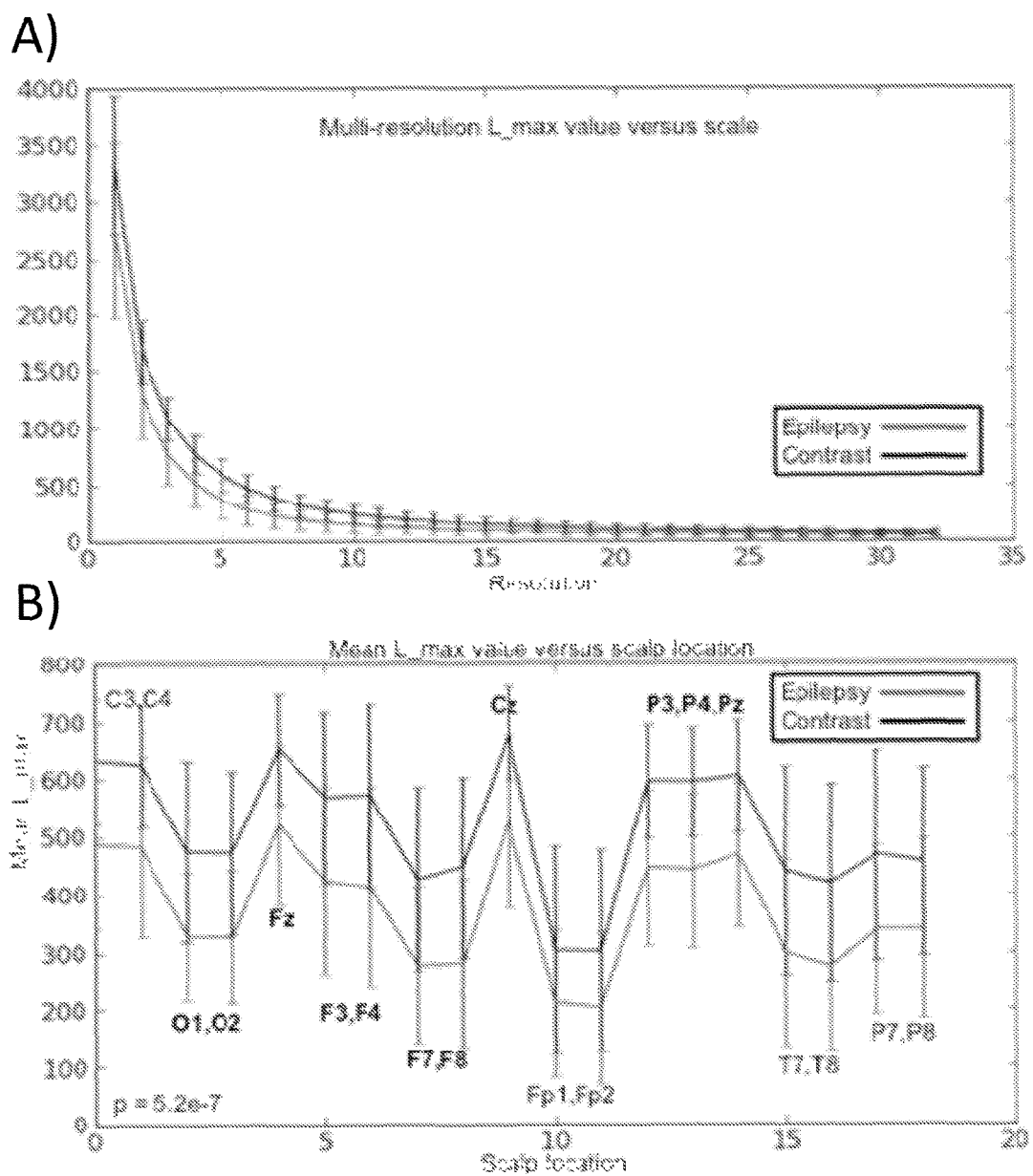
FIGS. 15A and 15B illustrate, respectively, multiresolution curves for L_max values, and group mean L_max values averaged across all scales for each channel location.

The multiresolution coarse-graining procedure described above (e.g., see Costa et al., 2005) was used to compute 32 multiresolution time series from the original. FIG. 15A illustrates multiresolution curves for the non-linear feature L_max averaged over the entire scalp. The area under the multiresolution curve for each scalp location was used to construct the plots shown in FIG. 15B, which shows group mean L_max values averaged over all scales for each channel location.

Recurrence plot (RP) values were computed for all of the scales derived from each EEG channel. In this implementation, six recurrence plot values were used in the analysis (RR, DET, LAM, L_max, L_mean and TT). The set of six values computed on all scales (1 to 32) for each subject at each EEG electrode constituted the feature set for that patient. Before feature selection and classification, all features were normalized to the range [0,1] over the set of all subjects and scales. These features are referred to as multiscale recurrence plot or MRP values.

Before machine classification, group differences for each of the MRP values at each scalp location were tested for significance. Bonferroni correction is used to determine a significance threshold for each RP value and sensor location. A strict application of Bonferroni correction requires that the variables be independent, which was not the case in this implementation. The values at each channel location are highly correlated with neighboring values, and the different RP values may be correlated for some complex systems. Nevertheless, this represents a useful criterion for examining which features may be the most useful for differentiating groups.

Values at different scales are highly correlated for the same measure and channel location, as illustrated in FIG. 15A. The mean area under the multiscale curve for each EEG sensor location and RP measure was computed. The area under each curve as illustrated in FIG. 15A is the multiscale recurrence plot value for each sensor location and each RP measure. Group means were then computed, along with p-values for the significance of the group differences. Group means over the entire scalp for each MRP value were also calculated. Since 19 channels and 6 RP values were used, a Bonferroni-corrected threshold of $0.05/(19*6)=4.4e-4$ was used as a simple test to determine which features were significantly different between the epilepsy and contrast groups. For scalp means, the Bonferroni correction was $0.05/6=8.0e-3$, since the channels were lumped together.

In this implementation, feature selection was performed using a simple ranking approach initially developed for high dimensional data sets, such as gene expression arrays (e.g., see Haury et al., 2011; Zhou and Wang, 2007). The feature set included 6 nonlinear recurrence plot variables as described above. Each value was computed across 19 channels at different scalp locations, as depicted in FIG. 4 and on 32 scales using the multiscaling technique described above.

Several different learning methods were tested, including k nearest neighbors (knn), naïve Bayes (bayes), decision trees (tree), random forests and support vector machines (svm). A stacking method that combines several learning methods was also used to remove biases from any one method. Classification accuracy, sensitivity and specificity were within several percentage points using all methods. Results were similar for the different methods. Values for the stacking method that combined knn, bayes, tree and svm are shown in Table 9, discussed in more detail below.

The statistical significance of the classification accuracy was assessed empirically using the permutation strategy discussed above. If the class labels are randomly permutated, a new classification accuracy can be computed using 10-fold cross validation. Accuracies were computed in this way for a large number of randomly-shuffled trials. The p-value was determined by counting the number of random classifications for which the accuracy was equal to or higher than the accuracy for the true labels.

Results produced by applying the methods in accordance with the above-described validation implementation are discussed in more detail below. Recurrence plot analysis of EEG data becomes much more useful if patterns can be found in the variables, considered as a single 'pattern', that reliably detect epilepsy and distinguish it from controls or, even more, distinguish different epilepsy cases. Machine learning algorithms are useful for this purpose. For machine learning classification, no significance threshold is applied to features, so the independence requirement is irrelevant. Rather, the permutation strategy described above may be used. In particular, machine learning classification is capable of finding arrangements or patterns among variables that may not be significantly different alone, but collectively, become significant when considered as a single whole entity or pattern. An analogy is that the black and white pixels that make up the letter 'a' and the letter 'z' may not be significantly different in images of these two letters, but the geometrical arrangement of the pixels is significantly different.

As shown in Table 9, three of the RP scalp-mean values are significantly different in the absence and contrast groups: L_max, L_mean and TT. The individual channels that meet the more strict significance threshold are listed in the second column of Table 9 for each MRP measure. L_entr is different when summed over the entire scalp, but not at any specific location using Bonferroni-corrected significance tests.

TABLE 9

The mean value for each of the measures over all resolutions and all scalp locations is significantly different.

| RP measure | Significant Channels[2] | p-value[1] (for mean over scalp) | Mean (std) Contrast | Mean (std) Absence |
|---|---|---|---|---|
| L_max | F3, F4, F7, F8, C3, C4, P3, P4, O1, O2, Fz, Cz, Pz | 5.19e−7 | 359.4 (73.9) | 260.5 (82.9) |
| L_mean | F7, F8 | 1.9e−3 | 9.19 (3.93) | 6.71 (2.87) |
| TT | F7, F8, Pz | 2.1e−3 | 13.93 (6.3) | 10.02 (4.58) |
| L_entr | — | 4.5e−3 | 2.11 (0.26) | 1.9 (0.31) |
| DET | — | 0.012 | 0.67 (0.016) | 0.655 (0.038) |
| RR | — | 0.61 | 0.38 (0.11) | 0.36 (0.12) |

[1]The significance level for the mean over the entire scalp is set at 0.05/6 measures = 8.3e−3.
[2]The significance level for individual channels is set at 0.05/(19 channels * 6 measures) = 4.4e−4.

The variables that are most significantly different between the absence and contrast groups in this implementation were L_max, L_mean and TT. The meaning of these variables in the context of complex dynamical systems is discussed briefly below.

L_max, the maximal diagonal line length in the recurrence plot, is related to the largest Lyapunov exponent of a chaotic signal, which is a dynamic complexity measure that describes the divergence of trajectories starting at nearby initial states, a measure of how chaotic a time series is. Lower values may be associated with greater synchronization.

L_mean, the average diagonal line length, is the average time that two time series of the trajectory are close to each other, and can be interpreted as the mean prediction time. Lower values may be associated with higher synchronization likelihood.

TT or trapping time, is a measure of the length of time that the system remains in a stable dynamical state. Lower TT values are an indication of more frequent transitions between states in a dynamical system.

Figure 16:
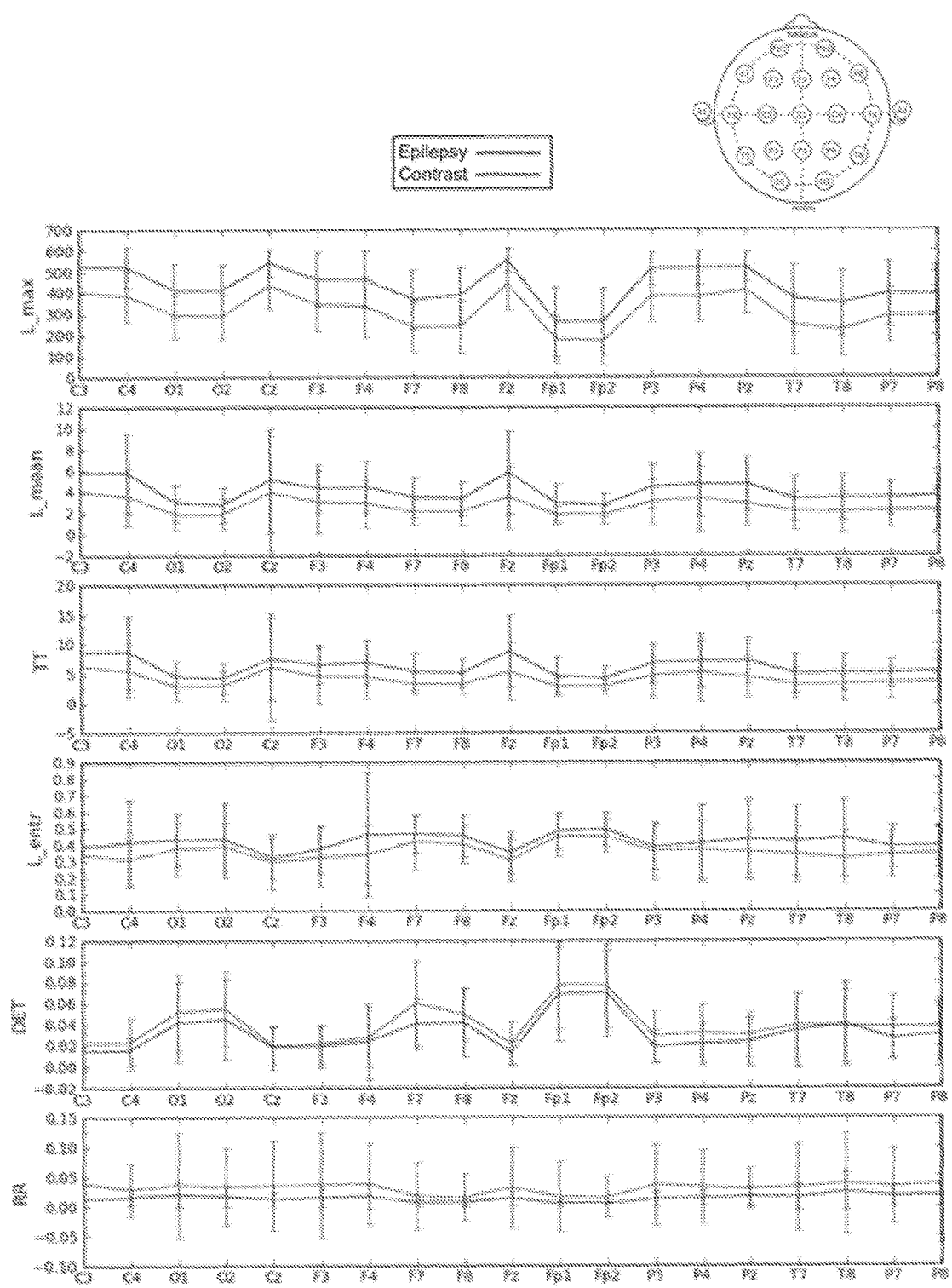
FIG. 16 illustrates group means for six recurrence plot (RP) measures at each scalp location.

Plots of each of the six RP measures at each scalp location are shown in FIG. 16. The shape of the curves for each group, absence or contrast, shows similar regional differences. For example, L_max is quite low at Fp1 and Fp2 compared to values in the parietal region (P3, P4 and Pz).

Figure 17:
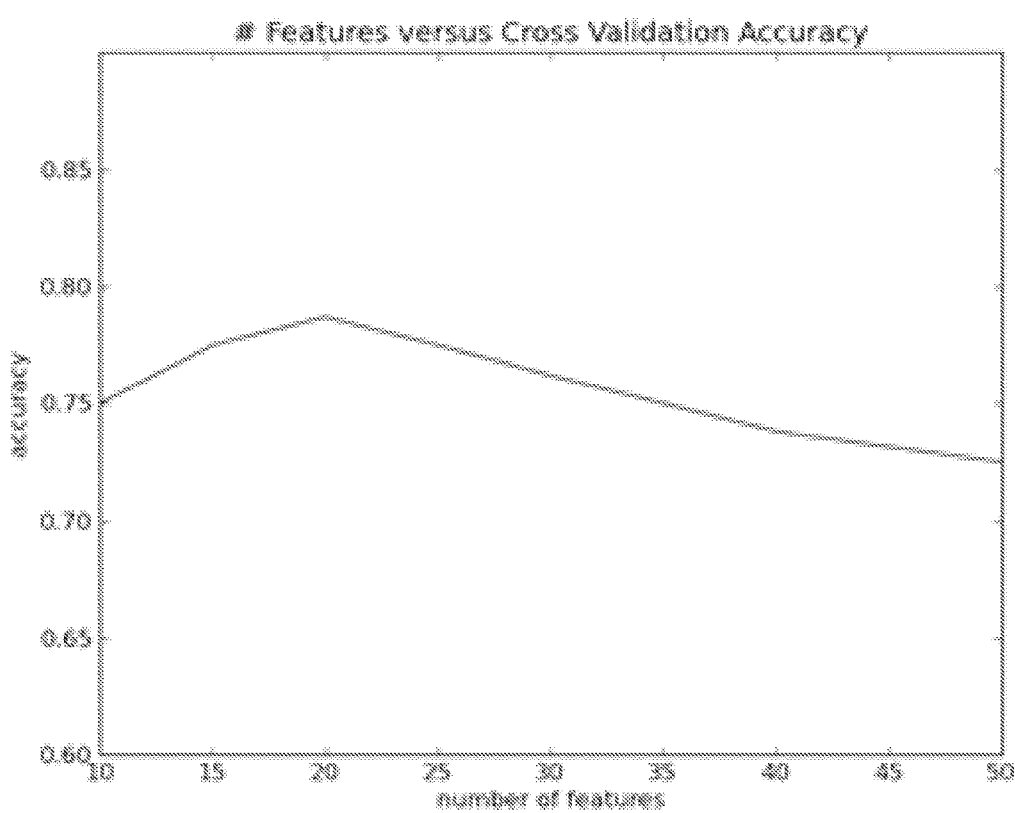
FIG. 17 illustrates cross validation accuracy with a support vector machine (SVM) classifier plotted against the number of features.

While significant group differences may give some insight into the neurophysiological meaning of the individual values, significant differences that are based on multivariable interactions or patterns are more difficult to find. To explore the possible value of MRP values for detecting the predisposition to have seizures, in this implementation, a machine classification approach was used. The feature selection method discussed above was used to select a number of features for classification that is appropriate for the relatively small population sample size (eighty patients total). As shown in FIG. 17, the cross validation accuracy declines slowly as the number of features used for classification increases past twenty. FIG. 17 shows a 10-fold cross validation accuracy for absence versus contrast groups with a support vector machine (SVM) classifier plotted against the number of features used. Features for classification were ranked using the ranking scheme described above. As the number of features used for classification increases, the 'curse of dimensionality,' described above, causes a decline in accuracy even though more information is available.

Table 10 shows cross validation results for absence epilepsy cases versus contrast for several different classification algorithms, using the twenty highest ranking features for the classification. The control group consisted of patients without epilepsy, but possibly having other neurological conditions that overlap with comorbid conditions shared by the epilepsy patients. The stack classifier was constructed by merging the other four classifiers (svm, knn, bayes, forest), producing an averaged result. The SVM results, in particular, are discussed in more detail below.

TABLE 10

Classification accuracy for absence epilepsy cases (n = 45) and contrast group (n = 35) using several different classifiers. The contrast group is composed of patients examined in the BCH Epilepsy Clinic who were determined to not have epilepsy.

| Learner | Accuracy | Sensitivity | Specificity | AUC | Empirical p-value |
|---|---|---|---|---|---|
| svm | 0.787 | 0.822 | 0.743 | 0.831 | 0.00 |
| knn | 0.662 | 0.711 | 0.600 | 0.779 | 0.00 |
| Naïve Bayes | 0.800 | 0.800 | 0.800 | 0.875 | 0.00 |
| Random forest | 0.700 | 0.689 | 0.714 | 0.802 | 0.00 |
| stack | 0.775 | 0.711 | 0.857 | 0.805 | 0.00 |

The significance of a cross validation classification was estimated using the method of random shuffling of labels, as described above. In this procedure, class labels (epilepsy or contrast group) are randomly shuffled, with all data features remaining unchanged. The classification procedure was then performed: features are ranked and the twenty highest were used in a 10-fold cross validation calculation to determine the classification accuracy. The shuffled cross validations were performed a large number of times and the fractional number of times the accuracy exceeds the accuracy determined with correct labels was the estimated p-value. The reported p-values of 0.0 in Table 10 indicate that in 100 trials, the accuracy with shuffled labels never equaled or exceeded the accuracy of the true classification, indicating that the classification accuracies are not likely to have been obtained by random chance alone.

Figure 18:
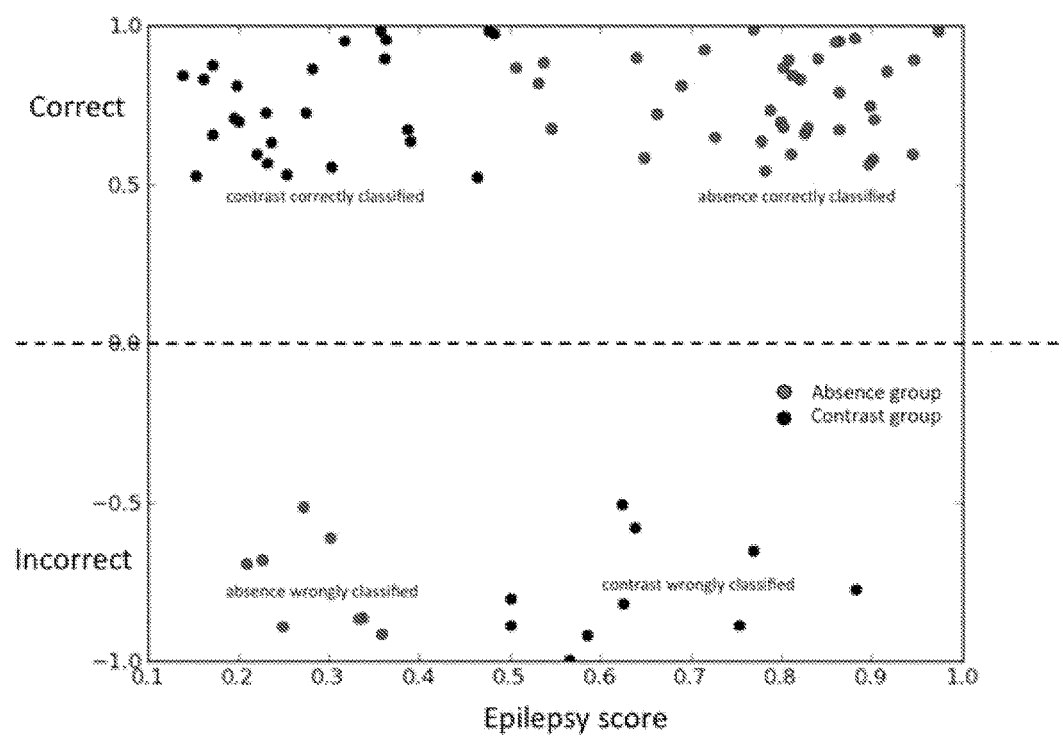
FIG. 18 illustrates a location of each subject relative to a dividing plane computed by an SVM classifier in accordance with some embodiments of the invention.

Classification with SVM determines a hyperplane that maximally separates the classification groups, which can be useful for measuring the distance of individual members from the dividing hyperplane. As shown in FIG. 18, individual subjects are plotted to illustrate this separation. The horizontal axis is a relative "epilepsy" score ranging from 0 (no epilepsy, maximum distance from epilepsy group) to 1 (maximum epilepsy score). Such scoring may be useful to determine correlations between distance from the dividing plane and the severity of epilepsy, for example. FIG. 18 illustrates the location of each subject relative to the dividing plane computed by the SVM classifier. Correctly classified points are in the upper half and incorrectly classified points in the lower half.

In the above-described validation implementation, significant group differences were found for the three features $L\_max$, $L\_mean$ and TT, even when a strict Bonferroni correction was applied. This result suggests that these values contain information that is significantly different in the absence epilepsy cases, even during non-spiking inter-ictal periods. In order to consider the recurrence plot feature set as a whole, a cross validation study was performed using several classification algorithms. Empirical p-values were used to test the significance of the classification results. A classification accuracy of 79% was obtained with an SVM classifier and similar accuracies were obtained with other classification methods. All results were found to be statistically significant when tested with random label shuffling.

An aim of the implemenations described herein was to determine if the dynamical measures computed from short EEG segments using multiresolution recurrence plot analysis would enable classification of absence epilepsy patients from controls. In the validation implementation, significant group differences were observed in several of the RP measures ($L\_max$, Lmean, and TT) at a number of scalp locations. Differences in $L\_max$ may reflect how easily nearby signals synchronize. Statistical feature selection was used to reduce the feature set for machine learning algorithms using a ranking approach that does not consider whether features are independent. Alternative feature selection techniques may also be used and the techniques described herein are not limited by the particular feature selection technique used. The derived classification accuracies may therefore be considered lower bounds, as alternative feature selection methods, or larger test populations that allow larger feature sets to be used, may increase classification accuracy. The analysis described herein for the validation implementation enabled classification with significantly good accuracy, sensitivity and specificity when compared to the gold-standard diagnosis (clinical history, physical exam and EEG interpreted by the epileptologist). Thus, further studies using MRP analysis as a means of identifying patients with a risk of having or developing seizures are warranted.

A seizure represents a brain state that has a high degree of periodicity and loss of complexity. Since seizures may involve a synchronization process that entrains multiple frequency bands leading to large amplitude, highly periodic and low complexity activity, it is speculated that the propensity to have seizures is represented by multiresolution dynamics. In biological systems, a lower level of chaotic dynamics is often associated with pathological conditions. Although the complete neurophysiological implications of recurrence plot analysis for physiological signals have not been extensively explored, some general meaning can be derived.

In the validation implementation, the maximum line length ($L\_max$) was found to be the most significantly different between the epilepsy and contrast groups. Thus, the lower Lmax values in the epilepsy group may be indications of a reduction in chaotic behavior. Lower values may be associated with a lower threshold for seizure initiation. Lower $L\_mean$ values appear to have a similar meaning in this context.

The trapping time variable (TT) is also generally lower in the epilepsy group. TT is an estimate of the time that a system will remain in a "trapped" state. Thus, lower TT values may be an indication of less stability in the system and more frequent transitions between dynamical states. Regional differences, as seen in the TT plots, may be useful for identifying epileptic tendencies in different regions of the brain.

The cross validation results discussed herein may be evidence that the MRP analysis extracts information from the MRP values that enables absence cases to be distinguished from controls with any of several classification methods. The low p-value found with randomized labels confirms that the information is significant.

The data discussed herein should be interpreted in the clinical setting from which data was acquired. For example, several potentially confounding factors may require further study. The contrast subjects in the validation implementation may have a variety of neurological disturbances that have not fully emerged. Contrast subjects presented in the clinic initially because of some neurological concerns. Thus, including a larger set of subjects, both controls without neurological impairments and confirmed absence epilepsy patients, will be helpful in determining the features that are most useful for detecting the presence of absence epilepsy and distinguishing absence epilepsy reliably from normal EEGs or other neurological conditions.

Additionally, the gender distribution between the absence and control cases in the illustrative implementations described above was quite different (67% males in the absence group versus 20% males in the control group). It is not known if this difference in gender distribution can affect epilepsy and classification results. Some studies of fractal dimension, a measure of signal complexity, in men and women suggest that EEG complexity is significantly higher in females. In a study using multiscale entropy to classify infant at high risk for developing autism (based on having an older sibling with autism), male and female differences in classification accuracy were found, suggesting that gender may play a role in detecting neurodevelopmental disorders. Thus, the role of gender should be investigated in future studies of epilepsy biomarkers.

Another factor for additional research is whether the MRP values discussed herein are detecting pathology that is specific to absence epilepsy or a more general neurological dysfunction. If MRP analysis is detecting the dynamics of an epileptic brain, then different epilepsies will reveal different spatial distributions than those seen for absence patients, and they should distinguish the different epilepsies.

In the implementations described herein, patients with absence epilepsy were selected because they represent a common diagnosis in the epilepsy population, are relatively easy to characterize clinically and electroencephalographically, and constitute one of the most homogeneous groups of patients with epilepsy. Additionally, there are no clear structural brain abnormalities on structural MRI imaging, and there is no EEG slowing which may confound results in other epilepsies or seizure types. However, it is expected that the techniques described herein may be useful for analyzing electromagnetic waveforms of patients with other types of epilepsy, and the techniques described herein are not limited for use with absence epilepsy detection.

The results discussed herein demonstrate that multiresolution dynamical analysis of EEG signals extracts information that provides information to classify absence epilepsy patients and controls using machine learning algorithms, and suggests that the MRP values may be useful as biomarkers for the detection of epilepsy. The sensor locations that are most useful for classification in our study population may suggest differences in brain function localization that is involved with seizure initiation in these patients. Larger sample sizes and further research in neurophysics, including network simulation, may be useful to determine the nonlinear physics that is responsible for the apparent usefulness of MRP analysis for detecting absence epilepsy in accordance with the techniques described herein.

Figure 14:
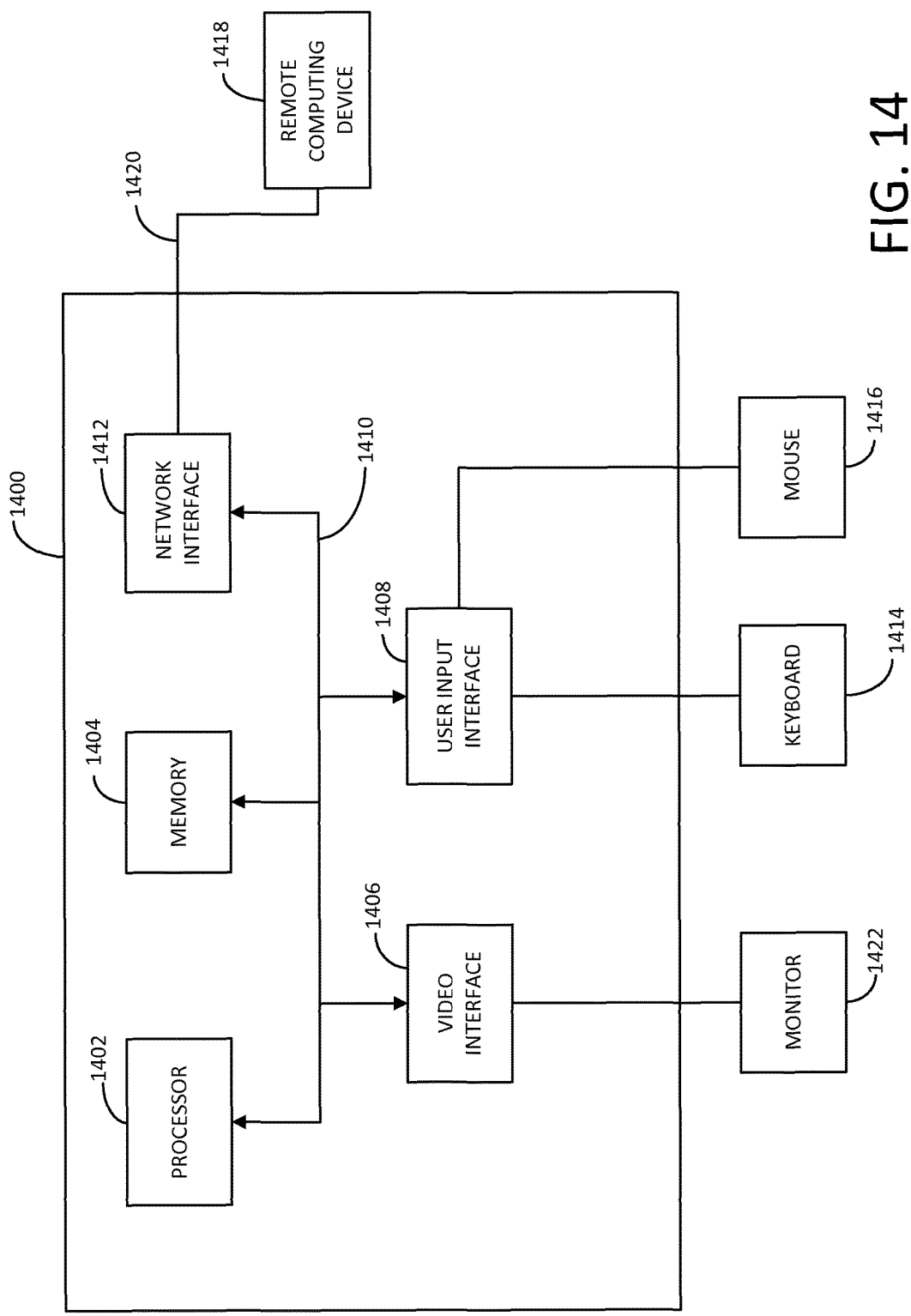
FIG. 14 is an exemplary computer system on which some embodiments may be implemented.

FIG. 14 shows a schematic block diagram of an illustrative computer 1400 on which features may be implemented. Only illustrative portions of the computer 1400 are identified for purposes of clarity and not to limit aspects of the invention in any way. For example, the computer 1400 may include one or more additional volatile or non-volatile memories, one or more additional processors, any other user input devices, and any suitable software or other instructions that may be executed by the computer 1400 so as to perform the function described herein. For example, the EEG data may be sent directly from a wireless EEG headset to a smartphone or cell phone and may be relayed directly to the remote computing device 1418.

In the illustrative embodiment, the computer 1400 includes a system bus 1410, to allow communication between a central processing unit 1402, a memory 1404, a video interface 1406, a user input interface 1408, and a network interface 1412. The network interface 1412 may be connected via network connection 1420 to at least one remote computing device 1418. Peripherals such as a monitor 1422, a keyboard 1414, and a mouse 1416, in addition to other user input/output devices may also be included in the computer system, as embodiments are not limited in this respect.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Through, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, embodiments may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect of this embodiment, one or more computer programs that when executed perform methods of embodiments need not reside on a single computer or processor, but may be distributed in a modular fashion amongst a number of different computers or processors to implement various embodiments.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationships between data elements.

Various aspects of embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

What is claimed is:

1. A method of treating a patient having epilepsy based on an quantitative assessment of an epileptogenicity level of the patient's brain, the method comprising:
    storing, in a database, a multi-dimensional dataset including non-linear feature set values for a first plurality of patients diagnosed with epilepsy and a second plurality of patients without an epilepsy diagnosis;
    receiving electroencephalography (EEG) data recorded from the brain of the patient, wherein the received EEG data includes a time series of EEG data that does not include and is not associated with epileptiform activity;
    generating, for the time series of EEG data that does not include and is not associated with epileptiform activity, a plurality of additional time series of EEG data by applying, using at least one computer processor, a multiscale algorithm to the time series of EEG data;
    calculating, for the time series of EEG data and each of the generated plurality of additional time series of EEG data, values for each of plurality of non-linear features in a set of non-linear features, wherein the set of non-linear features includes sample entropy and a plurality of recurrence quantitative analysis features;
    determining, using at least some of the calculated values for the plurality of non-linear features in the set of non-linear features, the multi-dimensional dataset stored in the database, and a statistical learning algorithm, the epileptogenicity level of the patient's brain; and
    treating the patient as a result of the determined epileptogenicity level.

2. The method of claim 1, wherein applying the multiscale algorithm comprises applying a wavelet transform to the received EEG data.

3. The method of claim 2, wherein the wavelet transform is a Haar wavelet transform with scales defined by factors of two.

4. The method of claim 1, wherein applying the multiscale algorithm comprises applying successive averaging of the received EEG data to create a coarse-grained time series.

5. The method of claim 1, wherein the plurality of recurrence quantitative analysis features includes recurrence rate, determinism, laminarity, or any combination thereof.

6. The method of claim 1, wherein the received EEG data does not include activity related to hyperventilation.

7. The method of claim 1, further comprising:
    recording the time series of EEG data from the brain of the patient.

8. The method of claim 1, wherein the time series of EEG data is at least ten seconds in duration.

9. The method of claim 1, further comprising:
    normalizing the calculated values for the plurality of non-linear features prior to using the calculated values to determine the epileptogenicity level of the patient's brain.

10. The method of claim 1, wherein the statistical learning algorithm uses a support vector machine classifier.

11. The method of claim 1, wherein the received EEG data comprises EEG data recorded from a plurality of channels, and wherein calculating values for each of a plurality of non-linear features in a set of non-linear features comprises calculating values for each of the plurality of non-linear features for each of the plurality of EEG channels of the received EEG data.

12. The method of claim 1, wherein the received EEG data comprises EEG data recorded from a plurality of channels, and wherein calculating values for each of a plurality of non-linear features in a set of non-linear features comprises calculating values for each of the plurality of non-linear features for a subset of the plurality of EEG channels of the received EEG data.

13. The method of claim 12, wherein the subset of the plurality of EEG channels includes a single EEG channel.

14. The method of claim 12, wherein the subset of the plurality of EEG channels includes less than all of the plurality of EEG channels.

15. The method of claim 1, further comprising:
    generating at least one scalp map, wherein the at least one scalp map is generated based, at least in part, on the calculated values for each of the plurality of non-linear features.

16. A non-transitory computer-readable medium, encoded with a plurality of instructions that, when executed by a computer, performs a method of selecting a treatment for a patient, the method comprising:
    storing, in a database, a multi-dimensional dataset including non-linear feature set values for a first plurality of patients diagnosed with epilepsy and a second plurality of patients without an epilepsy diagnosis;

generating, for a time series of electroencephalograpy (EEG) data recorded from the brain of the patient that does not include and is not associated with epileptiform activity, a plurality of additional time series of EEG data by applying a multiscale algorithm to the time series of EEG data;

calculating, for the time series of EEG data and each of the generated plurality of additional time series of EEG data, values for each of plurality of non-linear features in a set of non-linear features, wherein the set of non-linear features includes sample entropy and a plurality of recurrence quantitative analysis features;

determining, using at least some of the calculated values for the plurality of non-linear features in the set of non-linear features, the multi-dimensional dataset stored in the database, and a statistical learning algorithm, the epileptogenicity level of the patient's brain; and selecting a treatment for the patient as a result of the determined epileptogenicity level.

17. A computer system, comprising:

a database having stored thereon, a multi-dimensional dataset including non-linear feature set values for a first plurality of patients diagnosed with epilepsy and a second plurality of patients without an epilepsy diagnosis;

an input interface configured to receive electroencephalography (EEG) data recorded from a brain of a patient, wherein the received EEG data includes a time series of EEG data that does not include and is not associated with epileptiform activity;

at least one computer processor programmed to:

generate, for the time series of EEG data that does not include and is not associated with epileptiform activity, a plurality of additional time series of EEG data by applying a multiscale algorithm to the-time series of EEG data;

calculate, for the time series of EEG data and each of the generated plurality of additional time series of EEG data, values for each of plurality of non-linear features in a set of non-linear features, wherein the set of non-linear features includes sample entropy and a plurality of recurrence quantitative analysis features;

determine, using at least some of the calculated values for the plurality of non-linear features in the set of non-linear features, the multi-dimensional dataset stored in the database, and a statistical learning algorithm, the epileptogenicity level of the patient's brain; and select a treatment for the patient as a result of the determined epileptogenicity level; and an output interface configured to output an indication of the selected treatment.

* * * * *